United States Patent
Zander et al.

(10) Patent No.: US 7,145,054 B2
(45) Date of Patent: Dec. 5, 2006

(54) EMBOSSED ABSORBENT ARTICLE

(75) Inventors: Teresa Marie Zander, Bonduel, WI (US); Garry Roland Woltman, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/781,432

(22) Filed: Feb. 18, 2004

(65) Prior Publication Data
US 2005/0182374 A1 Aug. 18, 2005

(51) Int. Cl.
*A61F 13/533* (2006.01)
*A61F 13/15* (2006.01)

(52) U.S. Cl. .................... 604/380; D5/53; D24/125

(58) Field of Classification Search .............. 604/380, 604/385.01, 358; 428/98, 221; 602/41; D5/53; D24/124–126
See application file for complete search history.

(56) References Cited

U.S. PATENT DOCUMENTS

| | | | |
|---|---|---|---|
| 3,755,000 A * | 8/1973 | Demange | 429/40 |
| 3,860,004 A | 1/1975 | Nystrand | |
| 5,104,396 A | 4/1992 | Oatley et al. | |
| 5,858,515 A | 1/1999 | Stokes et al. | |
| 6,222,092 B1 * | 4/2001 | Hansen et al. | 604/378 |
| 6,312,416 B1 * | 11/2001 | Brisebois et al. | 604/385.01 |
| 6,319,239 B1 * | 11/2001 | Daniels et al. | 605/385.01 |
| D457,238 S | 5/2002 | Levy et al. | |
| 6,953,451 B1 * | 10/2005 | Berba et al. | 604/385.01 |
| 2002/0040212 A1 * | 4/2002 | Drevik | 604/380 |
| 2002/0143311 A1 * | 10/2002 | Brisebois | 604/385.01 |
| 2004/0176734 A1 * | 9/2004 | Rasmussen et al. | 604/380 |
| 2004/0254556 A1 * | 12/2004 | Brisebois et al. | 604/385.01 |

FOREIGN PATENT DOCUMENTS

| | | |
|---|---|---|
| DE | 36 20 077 A1 | 12/1987 |
| WO | WO 95/07674 A2 | 3/1995 |

OTHER PUBLICATIONS

Troitsky, M.S., D.Sc. *Stiffened Plates: Bending, Stability and Vibrations*, Elsevier Scientific Publishing Company, New York, 1976, pp. 63-64.

* cited by examiner

*Primary Examiner*—Tatyana Zalukaeva
*Assistant Examiner*—Laura C. Hill
(74) *Attorney, Agent, or Firm*—Paul Yee

(57) ABSTRACT

An article (20) comprises a deformation-control member which can include an extending medial section (38), and a selected stiffened region (34). The stiffened region (34) can include a first array (40) of individual, stiffening elements (35), and at least a second array (50) of individual, stiffening elements (37). In particular features, each of the first and second arrays (40, 50) of stiffening elements can have a convergently arranged nose-end (70, 78), and a relatively divergently arranged tail-end (74, 80). In another feature, the first and second arrays (40, 50) of stiffening elements (35, 37) can be configured to substantially avoid intersecting in the medial section (38) of the deformation-control member. In a further feature, the second array (50) of stiffening elements (37) can have a counter-positioned configuration relative to the first array (40) of stiffening elements (35).

26 Claims, 22 Drawing Sheets

EMBOSSED ABSORBENT ARTICLE

FIELD OF THE INVENTION

The present invention relates to an absorbent article. More particularly, the present invention pertains to an absorbent system for a feminine care article, such as an absorbent feminine care pad.

BACKGROUND OF THE INVENTION

Absorbent products intended to absorb discharged body fluids are well known in the art. Such absorbent products generally comprise a fibrous mass or other absorbent body which can absorb and hold the body fluids. Similarly, it is well known that, feminine care articles have been employed to absorb and hold liquids, such as urine and/or menses. The absorbent articles have included various systems of liquid-handling layers, such as intake layers, distribution layers, retention layers and the like. Additionally, the absorbent articles have included patterns of embossments distributed on the bodyside surface of the article to provide a hinging action, or to inhibit or direct a desired flow of liquids. Other arrangements of the absorbent articles have included wing portions which can help to hold the article in place at a selected location in a wearer's undergarment. Various fasteners have been employed to secure the wing portions in a desired configuration during ordinary use. The fasteners have included adhesive fasteners as well as mechanical fasteners, and the mechanical fasteners have included conventional, hook-and-loop fasteners.

Conventional absorbent systems, however, have not provided desired combinations of comfort, rapid intake of liquid, low surface staining, low leakage and surface dryness. When such conventional absorbent systems have been constructed to include embossments, the embossments have not been sufficiently effective during ordinary use, and the liquid-handling properties of the article have not provided desired levels of liquid distribution. As a result, there has been a continued need for absorbent articles having improved deformation-control systems and improved liquid-distribution systems that can provide more secure levels of liquid intake and storage, along with increased levels of confidence to the wearer.

BRIEF DESCRIPTION OF THE INVENTION

Generally stated, the present invention provides a distinctive article, which in particular configurations, may be an absorbent, feminine care article. The article comprises a deformation-control member which can include a medial section, and a selected stiffened region. The stiffened region can include a first array of individual, stiffening elements, and at least a second array of individual, stiffening elements. Each of the first and second arrays of stiffening elements can have a convergently arranged nose-end, and a relatively divergently arranged tail-end. In a particular feature, the first and second arrays of stiffening elements can be counter-positioned. In other features, each nose-end can be positioned toward a central region of the article, and each tail-end can be positioned toward an end region of the article. In still other features, each nose-end can be positioned toward an end region of the article, and each tail-end can be positioned toward a central region of the article. A further feature can include first and second arrays of stiffening elements that are configured to substantially avoid intersecting in the medial section of the deformation-control member. In still another feature, the deformation-control member can be an appointed shaping layer in an absorbent body. Other desired configurations of the invention can include a liquid-permeable cover, a baffle, and an absorbent body which is operatively sandwiched between the cover and baffle.

By incorporating its various aspects and features, the article of the invention can, for example, provide a distinctive configuration of embossments or other stiffening elements that can better produce a desired deformation of the article and can better maintain a desired article shape. In particular arrangements, the article of the invention can provide an article-deformation which can better conform to the contours of the wearer's body. The article of the invention can also provide an improved pattern of embossments or other surface contours that can better provide an improved direction and regulation of liquid flow, and can help move liquid away from the cover. The article can be less susceptible to premature leakage, and can provide greater protection and confidence to the wearer. Particular features can provide improved aesthetics and visual cues or indicators of absorbency and leakage protection.

BRIEF DESCRIPTION OF THE DRAWINGS

The various features, aspects and advantages of the present invention will become better understood with reference to the following description, appended claims and accompanying drawings where:

DETAILED DESCRIPTION OF THE INVENTION

Figure 1:
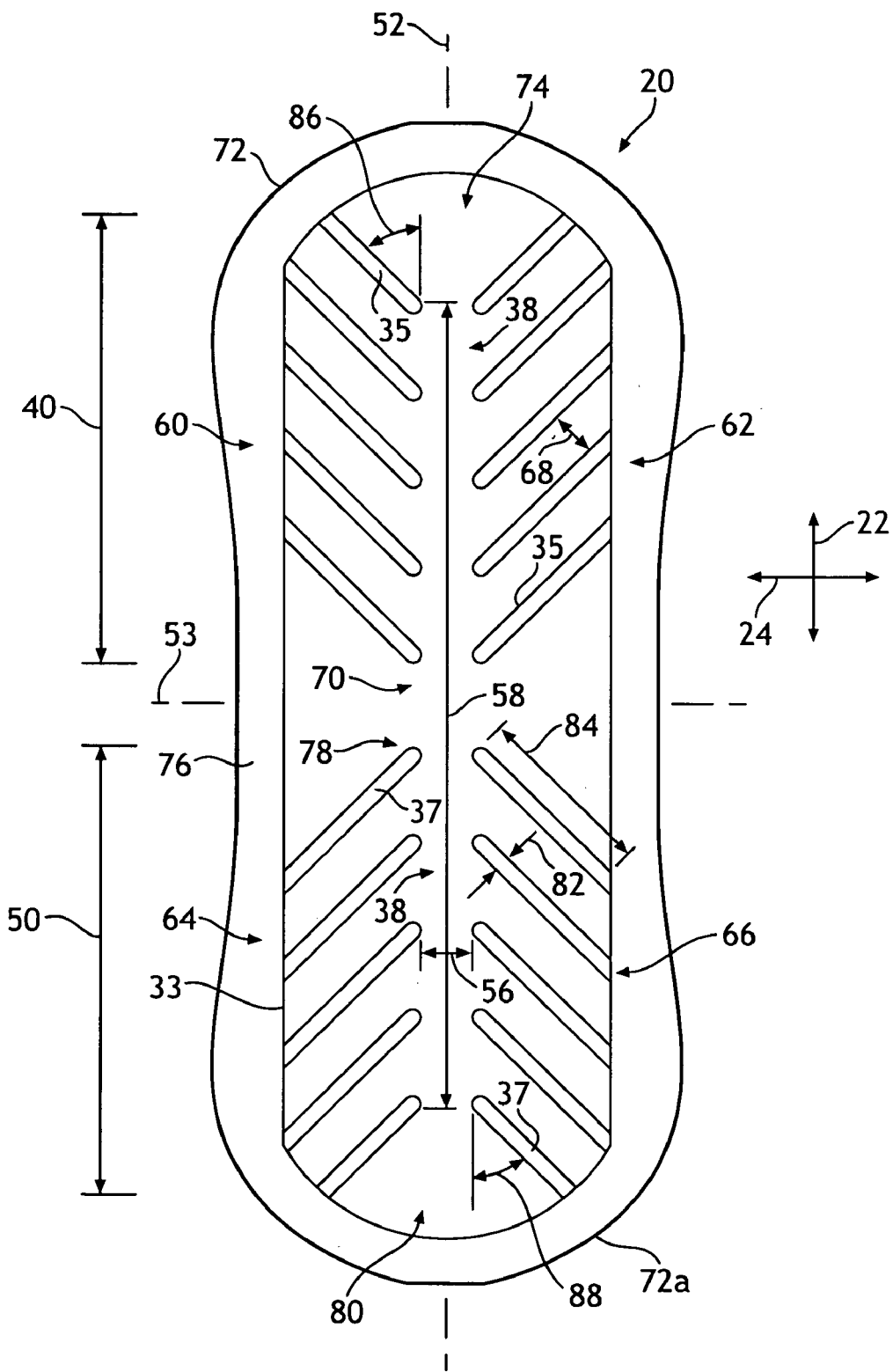
FIG. 1 shows a representative, top plan view of an article having a deformation-control member which includes counter-positioned arrays of stiffening elements.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

By the terms "particle," "particles," "particulate," "particulates" and the like, it is meant that the material is generally in the form of individually separate, discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like. Additionally, a particle, particulate or any desired agglomeration thereof may be composed of more than one type of material.

As used herein, the term "nonwoven" refers to a fabric web that has a structure of individual fibers or filaments which are interlaid, but not in an identifiable repeating manner.

As used herein, the terms "spunbond" or "spunbonded fiber" refer to fibers which are formed by extruding filaments of molten thermoplastic material from a plurality of fine, usually circular, capillaries of a spinneret, and then rapidly reducing the diameter of the extruded filaments.

As used herein, the phrase "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers.

"Coform" as used herein is intended to describe a blend of meltblown fibers and cellulose fibers that is formed by air forming a meltblown polymer material while simultaneously blowing air-suspended cellulose fibers into the stream of meltblown fibers. The meltblown fibers containing wood fibers are collected on a forming surface, such as provided by a foraminous belt. The forming surface may include a gas-pervious material, such as spunbonded fabric material, that has been placed onto the forming surface.

As used herein, the phrase "complex liquid" describes a liquid generally characterized as being a viscoelastic liquid comprising multiple components having inhomogeneous physical and/or chemical properties. It is the inhomogeneous properties of the multiple components that challenge the efficacy of an absorbent or adsorbent material in the handling of complex liquids. In contrast with complex liquids, simple liquids, such as, for example, urine, physiological saline, water and the like, are generally characterized as being relatively low-viscosity and comprising one or more components having homogeneous physical and/or chemical properties. As a result of having homogeneous properties, the one or more components of simple liquids behave substantially similarly during absorption or adsorption, although some components of the simple liquids may be absorbed or adsorbed more readily than others.

Although a complex liquid is generally characterized herein as including specific components having inhomogeneous properties, each specific component of a complex liquid generally has homogeneous properties. Consider for example a representative complex body-liquid having three specific components: red blood cells, blood protein molecules and water molecules. Upon examination, one skilled in the art could easily distinguish between each of the three specific components according to their generally inhomogeneous properties. Moreover, when examining a particular specific component such as the red blood cell component, one skilled in the art could easily recognize the generally homogeneous properties of the red blood cells.

As used herein, the phrase "absorbent article" refers to devices which absorb and contain body liquids, and more specifically, refers to devices which are placed against or near the skin to absorb and contain the various liquids discharged from the body. The term "disposable" is used herein to describe absorbent articles that are not intended to be laundered or otherwise restored or reused as an absorbent article after a single use. Examples of such disposable absorbent articles include, but are not limited to: health care related products including surgical drapes, gowns, and sterile wraps; personal care absorbent products such as feminine hygiene products. (e.g., sanitary napkins, panbliners, tampons, interlabial devices and the like), infant diapers, children's training pants, adult incontinence products and the like; as well as absorbent wipes and covering mats.

Disposable absorbent articles such as, for example, many of the feminine care absorbent products, can include a liquid pervious topsheet, a substantially liquid impervious backsheet joined to the topsheet, and an absorbent core positioned and held between the topsheet and the backsheet. The topsheet is operatively permeable to the liquids that are intended to be held or stored by the absorbent article, and the backsheet may be substantially impermeable or otherwise operatively impermeable to the intended liquids. The absorbent article may also include other components, such as liquid wicking layers, liquid intake layers, liquid distribution layers, transfer layers, barrier layers, and the like, as well as combinations thereof. Disposable absorbent articles and the components thereof can operate to provide a body-facing surface and a garment-facing surface. As used herein, a body-facing or bodyside surface means that surface of the article or component which is intended to be disposed toward or placed adjacent to the body of the wearer during ordinary use, while the outward, outward-facing or garment-side surface is on the opposite side, and is intended to be disposed to face away from the wearer's body during ordinary use. Such outward surface may be arranged to face toward or placed adjacent to the wearer's undergarments when the absorbent article is worn.

With reference to FIG. 1, an article 20 can comprise a deformation-control member 33 which can include a medial section 38, and at least one, flexure-control, stiffened region. The deformation-control member can be provided by any operative layer of material. The layer may be composed of a single material or may be-a composite which includes a plurality of materials. The stiffened region of the deformation-control member can include a first array 40 of individual, stiffening elements 35, and at least a second array 50 of individual, stiffening elements 37. The stiffening elements can be configured to operatively increase a selected bending stiffness of the corresponding stiffened regions of the deformation-control member. As representatively shown, the first array 40 of stiffening elements 35 can have a first, convergently arranged nose-end 70, and a first, relatively divergently arranged tail-end 74. In a like manner, the second array 50 of stiffening elements 37 can have a second, convergently arranged nose-end 78, and a second, relatively divergently arranged tail-end 80. In a particular aspect of the invention, the first and second arrays of stiffening elements can also be distinctively counter-positioned relative to each other. More particularly, the second array 50 of stiffening elements 37 can be arranged in a longitudinally opposed, oppositely aligned, counter-position relative to the first array 40 of stiffening elements 35. In another aspect of the invention, the first and second arrays 40, 50 of stiffening elements 35, 37 can be configured to substantially avoid intersecting in the medial section 38 of the deformation-control member. In desired configurations, the stiffening elements can be configured to include particular alignment angles. Further aspects and features of the invention are set forth in the present disclosure.

By incorporating its various features, aspects and configurations, the article of the invention can provide a distinctive pattern of embossments or other stiffening elements that can better provide a more effective control of the deformation of the article during use. The deformation can better conform to the in-use shape of the article to the contours of the body of the wearer. The stiffening elements can also be configured to provide an improved control of the direction and control of the flow of liquid, and can more effectively move liquid away from the cover and into the absorbent structure. As a result, the article can be less susceptible to premature leakage. Additionally, the article can provide better comfort and fit, improved protection and increased confidence to the wearer. Particular features can provide improved aesthetics and visual cues of absorbency.

The representatively shown article 20 can have a longitudinal direction 22, a transverse cross-direction 24, a longitudinal centerline 52 and a transverse centerline 53. Additionally, the deformation-control member 33 can include a pair of longitudinally-opposed half-portions which are positioned on opposite sides of the transverse centerline 53. The first array 40 of stiffening elements 35 can be located in a corresponding first, longitudinal half-portion of the deformation-control member 33, and the second array 50 of stiffening elements 37 can be located in a corresponding second, longitudinal half-portion of the deformation-control member.

The first array 40 of stiffening elements 35 can have a first, convergently arranged nose-end 70, and a first, relatively divergently arranged tail-end 74. In a like manner, the second array 50 of stiffening elements 37 can have a second, convergently arranged nose-end 78, and a second, relatively divergently arranged tail-end 80. In a particular feature, the first array 40 of stiffening elements 35 can be arranged with the first nose-end 70 of the first array 40 positioned toward a central region of the article 20, and with the first tail-end 74 positioned toward the first end region 72 of the article 20. The second array 50 of stiffening elements 37 can be operatively counter-positioned by locating the second nose-end 78 of the second array 50 toward the central region of the article, and locating the second tail-end 80 toward a second end region 72a of the article. Accordingly, the first nose-end 70 of the first array 40 can be positioned to point toward the transverse centerline 53, and the second nose-end 78 of the second array 50 can also be positioned to point toward the transverse centerline.

Figure 10:
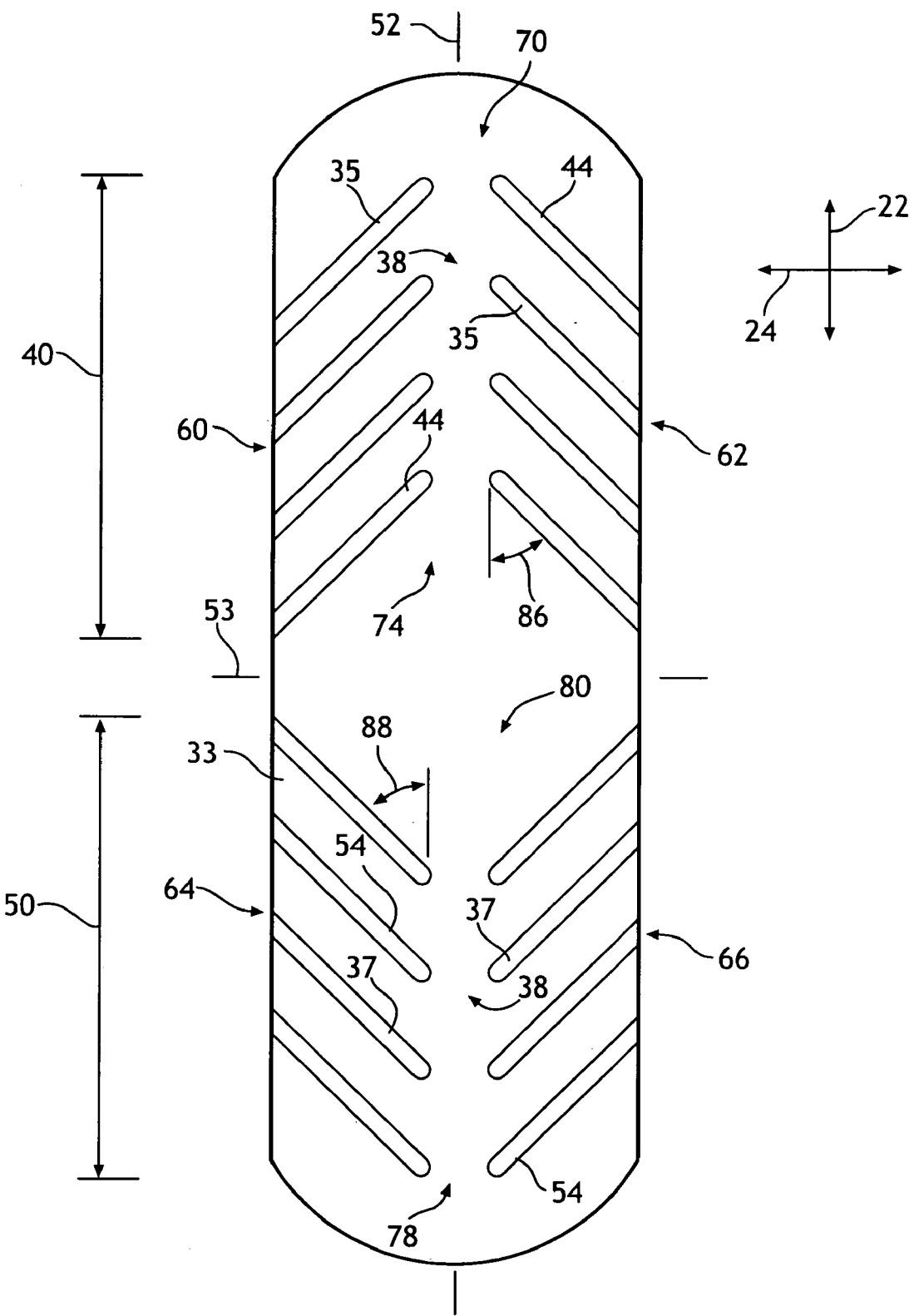
FIG. 10 shows a representative, top plan view of a deformation-control member which includes counter-positioned arrays of stiffening elements wherein converging nose-ends of the arrays are pointed toward end regions of the article.

In an optional configuration, the first nose-end 70 of the first array can be positioned toward a first end region 72 of the article 20, and the first tail-end 74 of the first array can be positioned toward the central region of the article 20 (e.g. FIG. 10). The second array can then be effectively counter-positioned by pointing the second nose-end 78 toward the second end region 72*a* of the article, and pointing the second tail-end 80 can toward the central region of the article. In desired configurations, the invention can be configured to provide a distinctive absorbent article.

The first array 40 can include a first base section 60, and a first complementary section 62. In a like manner, the second array 50 can include a second base section 64 and a second complementary section 66. Each base section 60, 64 is positioned laterally opposite to its corresponding complementary section 62, 66, respectively. According, each base section is positioned on an opposite side of the longitudinal centerline 52, relative to its corresponding complementary section. In a particular aspect, the pattern of stiffening elements can provide a first, generally fishbone array 40 of stiffening elements 35, and at least a second, generally fishbone array 50 of stiffening elements 37 in a second longitudinal half-portion of the deformation-control member. In another aspect, the stiffening elements can be distinctively angled. The stiffening elements can be configured to provide a distinctive region of controlled flexibility and controlled bending.

In the various arrangements of the article 20, the employed deformation-control member may be absorbent or substantially nonabsorbent, as desired. The flexure-control, stiffening elements can be provided by any structure that generates anisotropic mechanical properties in the flexure region where the axis of greatest stiffness is along the longitudinal axis of flexure-control element. These anisotropic constructions can include Natural features (material), Technical features (structural), and combinations of the Natural and Technical features. A natural anisotropic structure is intrinsically anisotropic due to the materials used to make the structure. A technical anisotropic structure is extrinsically anisotropic due to its geometric configuration of the structure. A combination anisotropic structure is both intrinsically and extrinsically anisotropic. See, for example, M.S. Troitsky, D. Sc.; Stiffened Plates: Bending, Stability, and Vibrations; pages 63–64, Elsevier Scientific Publishing Company; New York; N.Y. (1976).

Figure 2:
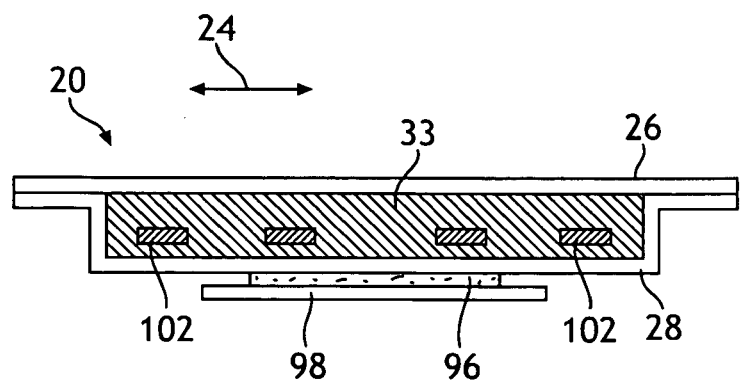
FIG. 2 shows a representative view of a transverse cross-section through an article having strips of stiffening material operatively joined with the deformation-control member.

Examples of natural anisotropic structures are composite materials that have stiffening members embedded or otherwise integrated into the material (e.g. FIG. 2). The flexure-control elements-can, for example, be provided by stiffening bars or strips that are embedded in the deformation-control member. In particular configurations, the stiffening elements can be provided by an array of separately provided strips of stiffening material, such as strips of deformable but relatively stiff plastic 102. The stiffening material is stiffer than the material of the deformation-control member with which the strips are operatively connected and attached.

Figure 2A:
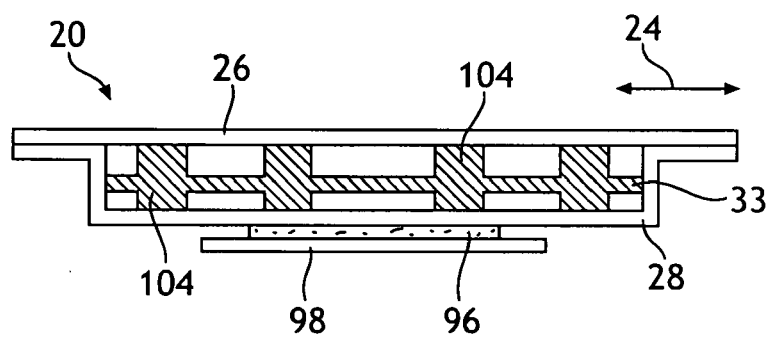
FIG. 2A shows a representative view of a transverse cross-section through an article having stiffening elements that are provided by relatively thicker regions of the deformation-control member.

An example of a technical anisotropic structure is a material that has non-planar geometric configuration (e.g. FIG. 2A). The flexure-control stiffening elements 35 can be provided by the regions in the cross-section of the material that are observed as being relatively thicker regions of the deformation-control member. The stiffening elements can optionally be provided by a distributed array of strip sections 104 wherein each strip section has a relatively higher basis weight or mass of material, as compared to areas of the deformation-control member that outside the strip section. In still other arrangements, the stiffening elements can be provided by a distributed array of corrugations that are formed with the material of the deformation-control member.

Figure 2B:
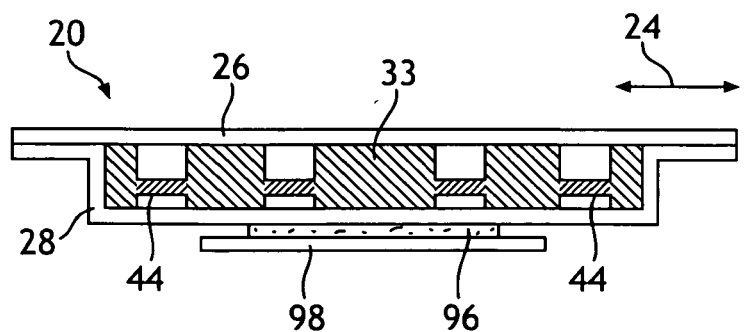
FIG. 2B shows a representative view of a transverse cross-section through an article having stiffening elements that are provided by embossed regions of the deformation-control member.

An example of a combination anisotropic structure is a uniform and planar material that has been selectively embossed to give a non-uniform and non-planar material. The flexure-control elements can be provided by more densified regions of the deformation-control member. The more densified regions may be thinner than the cooperating, less densified regions of the deformation-control member. As representatively shown in FIG. 2B, for example, the densified regions can be provided by a distributed array of embossments 44. In the immediate area of an individual embossment-element, the corresponding embossed material can have a basis weight that differs from or is substantially equal to that of an immediately adjacent area of unembossed material. Additionally, the embossed material may be compacted into a smaller thickness or volume and may be densified to a relatively greater density, as compared to an immediately adjacent area of unembossed or less-embossed material. Optionally, the embossed material may have a relatively greater density and approximately the same thickness, as compared to an immediately adjacent area of unembossed or less-embossed material.

In the various configurations of the article 20, it should be readily appreciated that the individual stiffening elements may have any operative shape or configuration. For example, the individual stiffening elements may have different lengths or substantially equal lengths along their longer dimension, and each stiffening element may be discontinuous or substantially continuous. Additionally, each individual stiffening element may be substantially straight, curvilinear, wavy, zig-zag, J-shaped, S-shaped or the like. Any combination of the above-mentioned features may also be employed.

The employed stiffening elements can, at least in part, operate to selectively increase a cross-directional bending stiffness value in the stiffened region of the selected deformation-control member. Accordingly, the stiffening elements can, at least in part, operate to selectively increase a bending stiffness of the stiffened region with respect to a bending-moment applied about a bending axis that is aligned generally parallel to a longitudinal direction 22. Additionally, an individual stiffening element can, at least in part, increase a bending stiffness along its lengthwise dimension. Accordingly, the individual stiffening element can also increase a bending stiffness of the stiffened region with respect to a bending-moment applied about a bending axis that is aligned generally perpendicular to the longer, lengthwise dimension of the stiffening element.

The deformation-control member may be a separately-provided component or an integrally-provided component of an absorbent article. In particular aspects, the deformation-control member can be provided by a selected portion or component of a personal care, absorbent article. As representatively shown in FIGS. 3 through 3C, for example, the deformation-control member can be provided by a selected portion of an absorbent body 30, and the absorbent body can be configured to provide a storage or retention portion that can hold and retain absorbed liquids, such as urine, vaginal fluid and/or menses.

In the present disclosure, the article 20 may be particularly discussed in the context of the configuration that has the deformation-control member provided by at least a selected portion of the representatively shown absorbent body 30. Additionally, the article may be discussed in terms of the configuration wherein the first array 40 of stiffening elements has been provided by the representatively shown embossment elements 44, and has the second array 50 of stiffening elements has been provided by the representatively shown embossment elements 54. It should be understood, however, that the descriptions, features and parameters made with reference to the absorbent body 30 (or any selected portion thereof) can also pertain to the other deformation-control members that may be employed by other arrangements of the present invention. Additionally, it should be understood that the descriptions, features and parameters made with reference to the embossment elements 44 and/or 54 can also pertain to the other configurations of the stiffening elements that may be employed by other arrangements of the disclosed invention.

Figure 4:
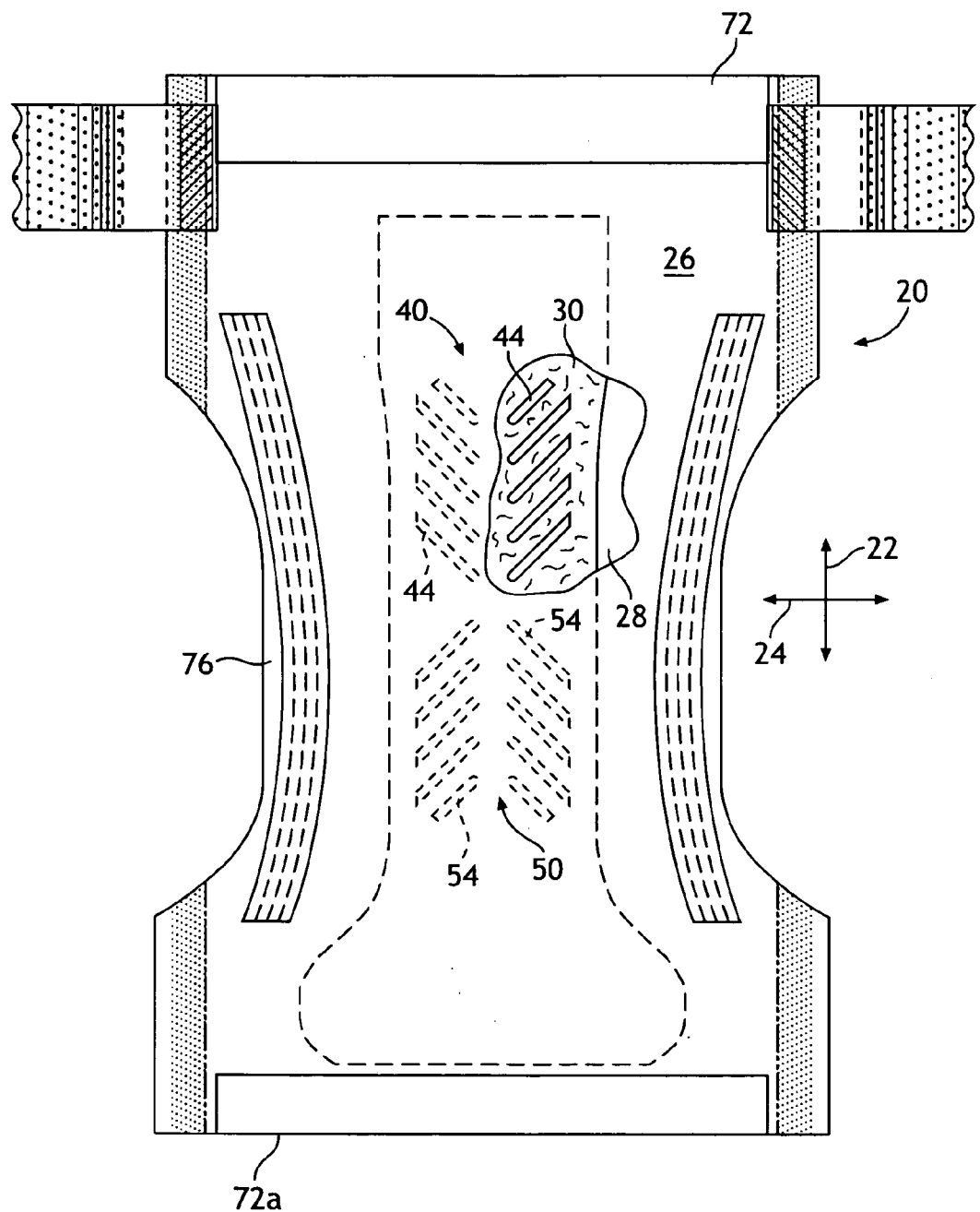
FIG. 4 shows a representative, partially cut-away, top plan view of the bodyside of a diaper article having an absorbent shaping layer, wherein the shaping layer provides a deformation-control member having counter-positioned arrays of stiffening elements.
Figure 5:
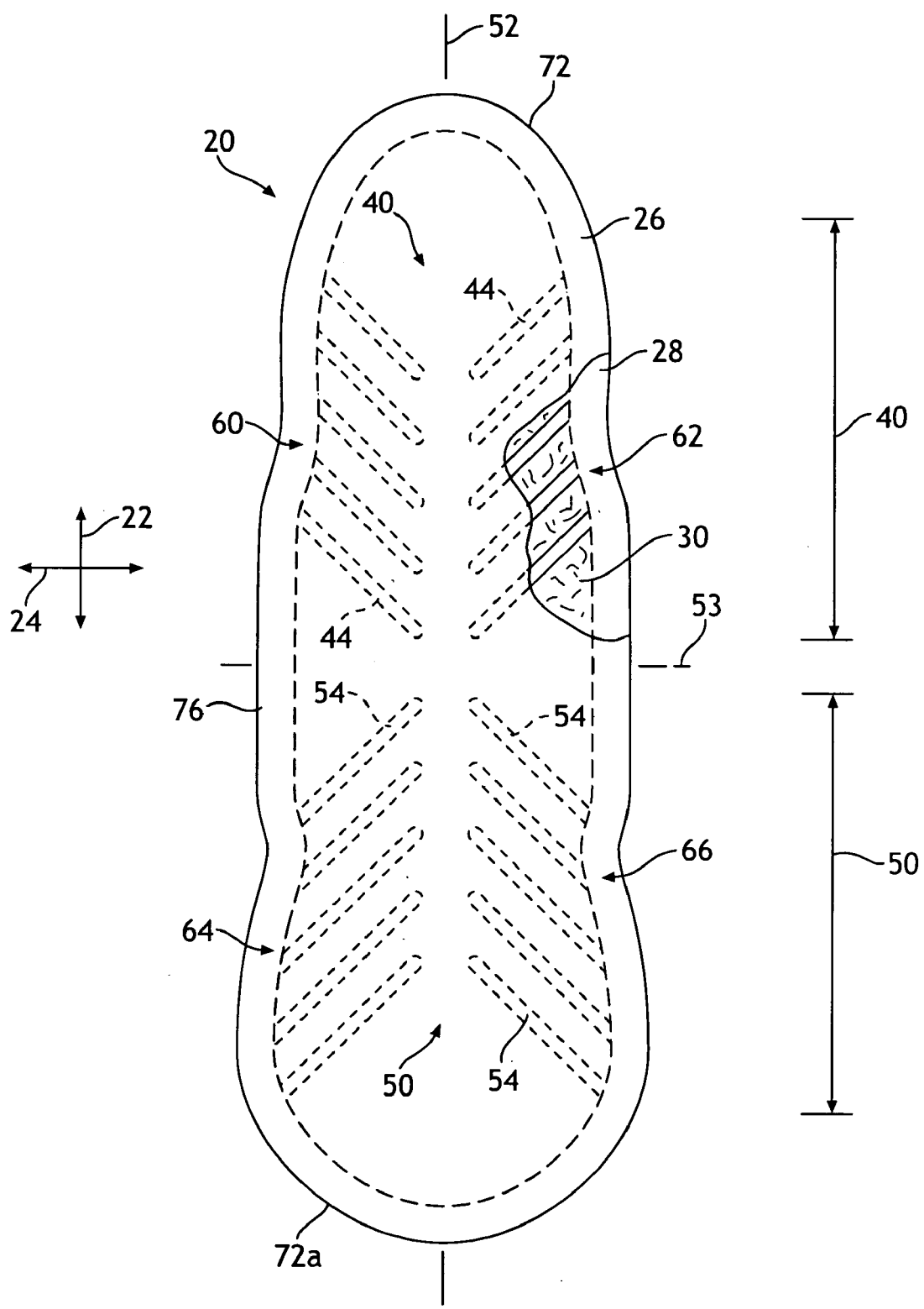
FIG. 5 shows a representative, partially cut-away, top plan view of the bodyside of a longitudinally non-symmetric article having an absorbent shaping layer, wherein the shaping layer provides a deformation-control member having counter-positioned arrays of stiffening elements.

In its various arrangements, a suitable article 20 can be configured to provide a personal care absorbent product, such as an infant diaper (e.g. FIG. 4), children's training pants, an adult incontinence product or the like. In desired configurations, the article 20 can provide a feminine hygiene product (e.g., a sanitary napkin, a pantiliner, an interlabial device or the like). As representatively shown, for example, the feminine care article can be a feminine care pad or napkin. The article can have a lengthwise, longitudinal direction 22 which can extend along an appointed y-axis of the article, and a transverse, laterally extending, cross-direction 24 which can extend along an appointed x-axis of the article. Additionally, the article can include first and second longitudinally opposed end portions 72, and an intermediate portion 76 located between the end portions. Generally stated, the intermediate portion 76 can be the middle 34 percent (%) of an overall, longitudinal length of the article 20. The article 20 can have any desired shape. The feminine care article can, for example, have a dog bone shape, a race track shape, an hourglass shape or the like. Additionally, the article can be substantially, longitudinally symmetric (e.g. FIGS. 3 and 6), or may be longitudinally asymmetric (e.g. FIG. 5), as desired.

As representatively shown, the longitudinal dimension of the article is relatively larger than the lateral dimension of the article. Particular configurations of the absorbent article can include a bodyside liner or cover 26 (also referred to as a topsheet), and a backsheet or baffle 28. Additionally, an absorbent structure 30 can be positioned between the cover and baffle. In desired arrangements, the cover can be liquid-permeable, and the baffle can be operatively liquid-impermeable. In other arrangements, the baffle can provide an outercover of the article. As representatively shown, for example, peripheries of the topsheet and backsheet may be substantially entirely coterminous. Alternatively, the peripheries of the topsheet 26 and the backsheet 28 may be partially or entirely non-coterminous.

The topsheet or cover 26 may include a layer constructed of any operative material, and may be a composite material. For example, the cover layer can include a woven fabric, a nonwoven fabric, a polymer film, a film-fabric laminate or the like, as well as combinations thereof. Examples of a nonwoven fabric include spunbond fabric, meltblown fabric, coform fabric, a carded web, a bonded-carded-web, a bicomponent spunbond fabric or the like as well as combinations thereof. Other examples of suitable materials for constructing the cover layer can include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof. In desired arrangements, the cover layer can be configured to be operatively liquid-permeable.

A more particular example of a suitable cover layer material can include a bonded-carded-web composed of polypropylene and polyethylene, such as has been used as a cover stock for KOTEX brand pantiliners, and has been obtainable from Vliesstoffwerk Christian Heinrich Sandler GmbH & Co. KG, a business having an address at Postfach 1144, D95120 Schwarzenbach/Saale, Germany. Other examples of suitable materials are composite materials of a polymer and a nonwoven fabric material. The composite materials are typically in the form of integral sheets generally formed by the extrusion of a polymer onto a web of spunbond material. In a desired arrangement, the cover layer 26 can be configured to be operatively liquid-permeable with regard to the liquids that the article is intended to absorb or otherwise handle. The operative liquid-permeability may, for example be provided by a plurality of pores, perforations, apertures or other openings, as well as combinations thereof, that are present or formed in the cover layer. The apertures or other openings can help increase the rate at which bodily liquids can move through the thickness of the cover layer and penetrate into the other components of the article (e.g. into the absorbent structure 30). The selected arrangement of liquid-permeability is desirably present at least on an operative portion of the cover layer that is appointed for placement on the body-side of the article. The cover layer 26 can provide comfort and conformability, and can function to direct bodily exudates away from the body and toward the absorbent structure 30. In a desired feature, the cover layer 26 can be configured to retain little or no liquid in its structure, and can be configured to provide a relatively comfortable and non-irritating surface next to the body-tissues of a female wearer. The cover layer 26 can be constructed of any material which is also easily penetrated by bodily fluids that contact the surface of the cover layer.

The cover 26 can also have at least a portion of its bodyside surface treated with a surfactant and/or a menses modifier to increase the surface energy of the material surface or reduce the viscoelastic properties of the menses, and to render the cover more hydrophilic and more wettable to body fluids. The surfactant can permit arriving bodily liquids to more readily penetrate the cover layer. The surfactant may also diminish the likelihood that the arriving bodily fluids, such as menstrual fluid, will flow off the cover layer rather than penetrate through the cover layer into other components of the article (e.g. into the absorbent body structure). In a particular configuration, the surfactant can be substantially evenly distributed across at least a portion of the upper, bodyside surface of the cover 26 that overlays the upper, bodyside surface of the absorbent.

The cover 26 may be maintained in secured relation with the absorbent structure 30 by bonding all or a portion of the adjacent surfaces to one another. A variety of bonding articles known to one of skill in the art may be utilized to achieve any such secured relation. Examples of such articles include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent.

The cover 26 typically extends over the upper, bodyside surface of the absorbent structure, but can alternatively extend around the article to partially or entirely, surround or enclose the absorbent structure. Alternatively, the cover 26 and the baffle 28 can have peripheral margins which extend outwardly beyond the terminal, peripheral edges of the absorbent structure 30, and the extending margins can be joined together to partially or entirely, surround or enclose the absorbent structure.

The baffle 28 may include a layer constructed of any operative material, and may or may not have a selected level of liquid-permeability or liquid-impermeability, as desired. In a particular configuration, the backsheet or baffle 28 may be configured to provide an operatively liquid-impermeable baffle structure. The baffle may, for example, include a polymeric film, a woven fabric, a nonwoven fabric or the like, as well as combinations or composites thereof. For example, the baffle may include a polymer film laminated to a woven or nonwoven fabric. In a particular feature, the polymer film can be composed of polyethylene, polypropylene, polyester or the like, as well as combinations thereof. Additionally, the polymer film may be micro-embossed. Desirably, the baffle 28 can operatively permit a sufficient passage of air and moisture vapor out of the article, particularly out of an absorbent (e.g. storage or absorbent structure 30) while blocking the passage of bodily liquids. An example of a suitable baffle material can include a breathable, microporous film, such as a HANJIN Breathable Baffle available from Hanjin Printing, Hanjin P&C Company Limited, a business having offices located in Sahvon-li.Jungan-mvu.Kongiu-City, Chung cheong nam-do, Republic of South Korea. The baffle material is a breathable film, which is dimple embossed and contains: 47.78% calcium carbonate, 2.22% TiO2, and 50% polyethylene.

In a particular feature, the polymer film can have a minimum thickness of no less than about 0.025 mm, and in another feature, the polymer film can have a maximum thickness of no greater than about 0.13 mm. Bicomponent films or other multi-component films can also be used, as well as woven and/or nonwoven fabrics which have been treated to render them operatively liquid-impermeable. Another suitable baffle material can include a closed cell polyolefin foam. For example, closed cell polyethylene foam may be employed. Still another example of a baffle material would be a material that is similar to a polyethylene film which is used on commercially sold KOTEX brand pantiliners, and is obtainable from Pliant Corporation, a business having offices located in Schaumburg, Ill., USA.

The structure of the absorbent body 30 can be operatively configured to provide desired levels of liquid retention and storage capacity, and desired levels of liquid acquisition and distribution. More particularly, the absorbent body can be configured to hold a liquid, such as urine, menses, other complex liquid or the like, as well as combinations thereof. As representatively shown, the absorbent body can include a matrix of absorbent fibers and/or absorbent particulate material, and the absorbent fiber can include natural and/or synthetic fiber. The absorbent body may also include one or more components that can modify menses or inter-menstrual liquids.

The absorbent structure 30 may also include superabsorbent material. Superabsorbent materials suitable for use in the present invention are known to those skilled in the art, and may be in any operative form, such as particulate form. Generally stated, the superabsorbent material can be a water-swellable, generally water-insoluble, hydrogel-forming polymeric absorbent material, which is capable of absorbing at least about 20, desirably about 30, and possibly about 60 times or more its weight in physiological saline (e.g. 0.9 wt % NaCl). The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors, such as the Dow Chemical Company and Stockhausen, Inc. The superabsorbent material may desirably be included in an appointed storage or retention portion of the absorbent system, and may optionally be employed in other components or portions of the absorbent article.

In desired configurations, the absorbent body 30 can be included in a feminine care article, and can be configured to provide any operative absorbent capacity. In particular arrangements, for example, the absorbent body can provide a total, overall absorbent saturation capacity of up to about 5 grams of menses simulant. In other arrangements, the absorbent body can provide a total, overall absorbent saturation capacity which is at least a minimum of about 5.5 grams of menses simulant (5.5 g). The overall saturation capacity can alternatively be at least about 25 g, and can optionally be at least about 40 grams of menses simulant to provide improved performance. In a desired arrangement the total saturation capacity of the absorbent body 30 can be up to about 107 grams of menses simulant, or more.

A suitable menses simulant is composed of swine blood diluted with swine plasma to provide a hematocrit level of 35% (by volume). A suitable device for determining the hematocrit level is a HEMATOSTAT-2 system, available from Separation Technology, Inc., a business having offices located in Altamonte Springs, Fla., U.S.A. Alternatively, a substantially equivalent device or system may be employed.

The specific saturation capacity and the specific retention capacity can be determined by soaking a 1 inch by 1 inch (2.54 cm×2.54 cm) sample of absorbent material in an amount of menses simulant that is sufficient to fully saturate the sample (e.g. 30 mL) for 30 minutes. The wet absorbent is then placed between a layer of through-air-bonded-carded web material and a layer of blotter paper, and a pressure of 0.05 psi (0.345 KPa) is applied for 1 minute to remove any pools of liquid. The saturated sample is then weighed. The weight of liquid held in the sample divided by the dry weight of the sample is the specific saturation capacity of the sample.

After the saturated sampled is weighed, the absorbent sample is placed in a centrifuge and spun at 300 G for 3 minutes. The spun sample is then weighed. The weight of the liquid remaining in the spun sample divided by the dry weight of the sample is the specific retention capacity of the sample.

Accordingly:

Saturation Capacity=(Wet Wt. Before Centrifuge−Dry Wt.)/(Dry Wt.)  a.

Retention Capacity=(Wet Wt. After Centrifuge−Dry Wt.)/(Dry Wt.)  b.

The total absorbent saturation capacity of an overall layer or other component can be determined by multiplying its specific saturation capacity times the total weight of such component. Similarly, total absorbent retention capacity of an overall layer or other component can be determined by multiplying its specific retention capacity times the total weight of such component.

A suitable through-air-bonded-carded web material has a 2.5 osy (84.8 g/m²) basis weight, a 0.024 g/cm³ density, and is composed of 60 wt % of 6 denier, KoSa type 295 polyester fiber; and 40 wt % of 3 denier, Chisso ESC-HR6 bicomponent fiber. The polyester fiber is available from KoSa, a business having offices located in Charlotte, N.C., U.S.A., and the bicomponent fiber is available from Chisso Corporation, a business having offices located in Osaka, Japan. A suitable blotter paper is 100-lb VERIGOOD white blotter paper available from Fort James Corporation, a business having offices located in Menasha, Wis., U.S.A. (e.g. product item number 411-01012). Equivalent materials may optionally be employed.

Figure 6:
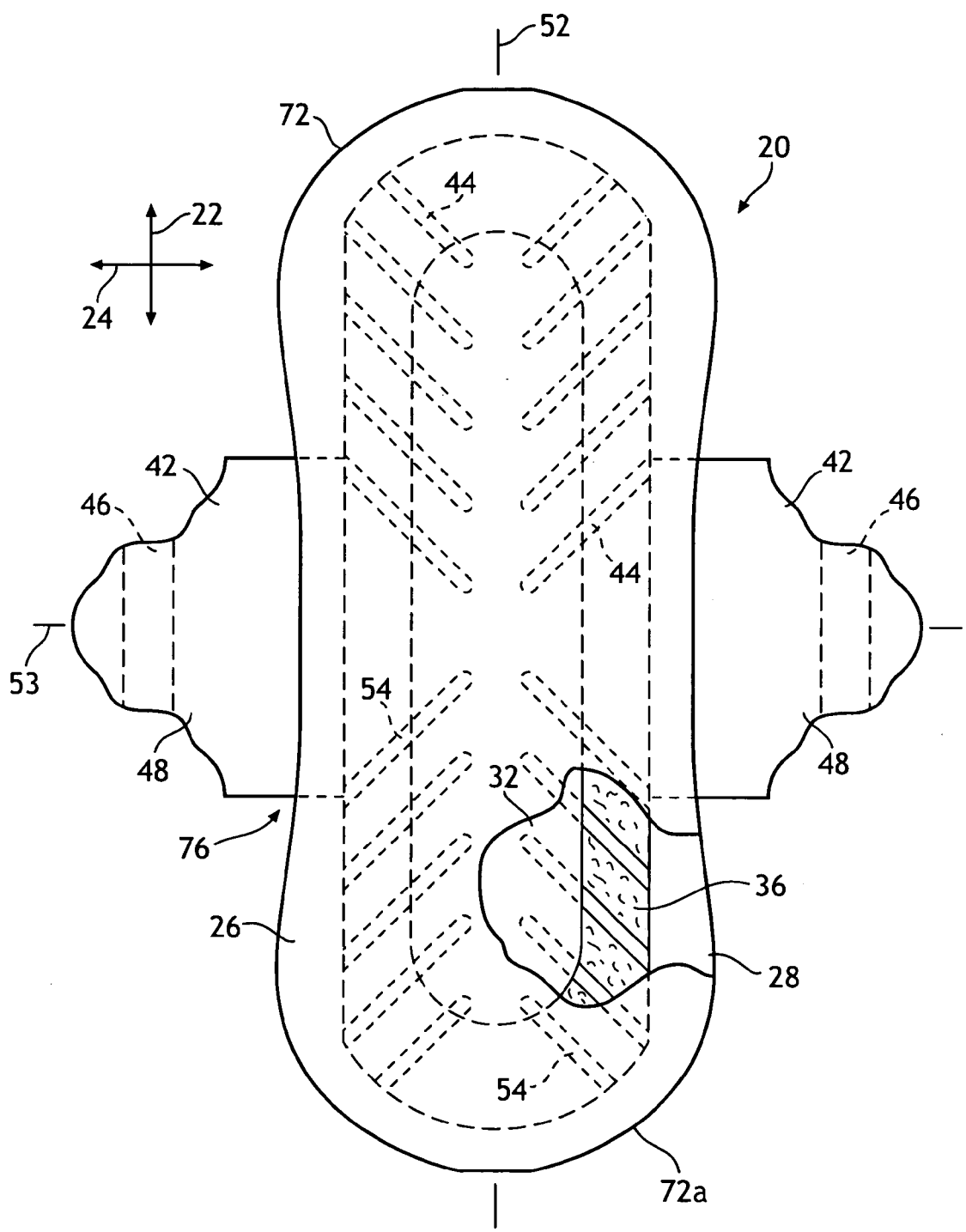
FIG. 6 shows a representative, partially cut-away, top plan view of the bodyside of another article having side-panel portions, and an absorbent structure with an intake layer and a shaping layer, wherein the shaping layer provides a deformation-control member having counter-positioned arrays of stiffening elements.
Figure 6A:
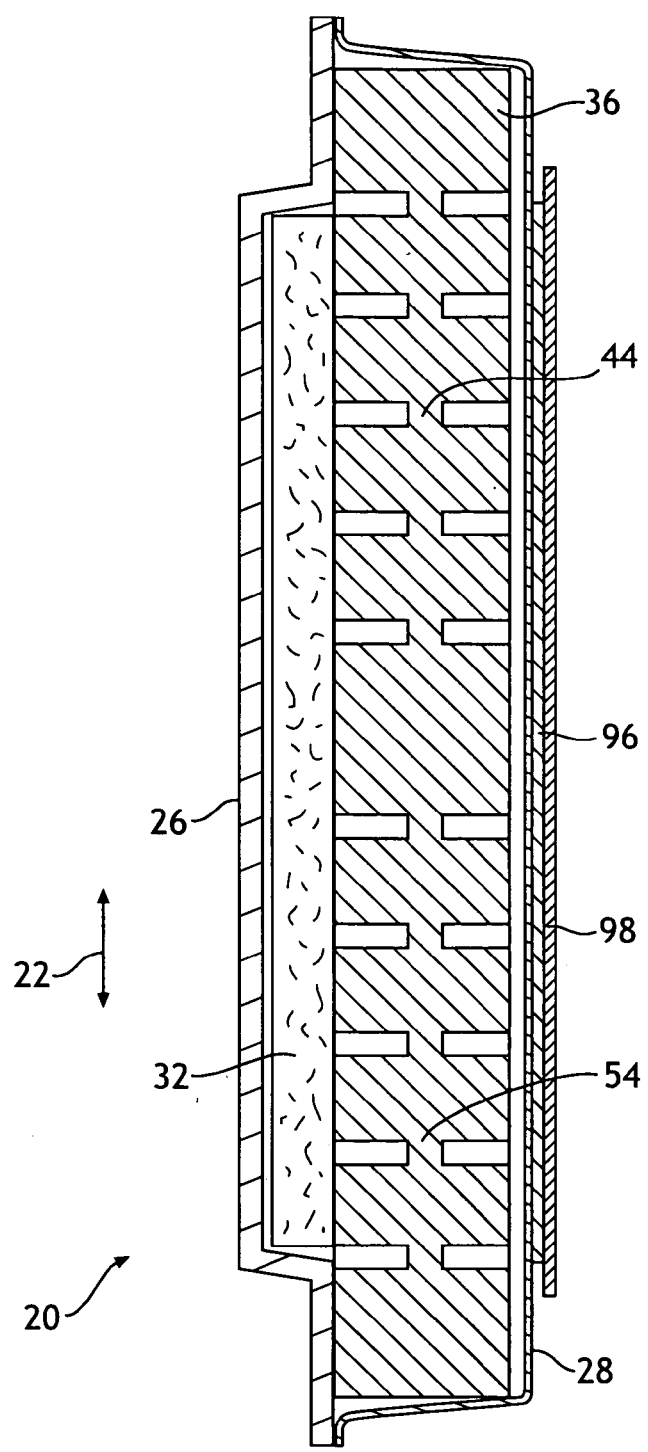
FIG. 6A shows a representative view of a longitudinal cross-section through an article which includes an intake layer and a shaping layer with embossed stiffening elements.

As representatively shown, the absorbent body 30 can be provided by a single unitary layer, or can comprise a composite structure having a selected plurality of component strata or layers. With reference to FIGS. 6 and 6A, for example, the absorbent body can include an intake layer 32 and a shaping layer 36.

The shaping layer 36 can be configured to be operatively absorbent, and the size of the shaping layer may or may not be coextensive with the size of the intake layer 32. As representatively shown, the shaping layer 36 can be constructed to provide a relatively larger component of the absorbent body, and the first and second arrays 40, 50 of embossment elements 44, 54 can be positioned and formed in the shaping layer. Any other desired components may also be operatively combined with the shaping layer 36 to form the desired absorbent structure. For example, the absorbent body can include a supplemental layer, such as provided by the representatively shown intake layer 32. The supplemental layer may be located generally adjacent a garment-facing side of the shaping layer 36. In a desired configuration, the supplemental layer, can be located generally adjacent a body-side of the shaping layer 36. The first and second arrays 40, 50 of embossment elements 44, 54 may or may not be located and formed in the supplemental layer, as desired.

As representatively shown, the shaping layer 36 can be an absorbent pad which is positioned between the cover 26 and the baffle 28, and the intake layer 32 can be positioned between the cover 26 and the shaping layer 36. In desired arrangements, the intake layer can be a separately provided absorbent pad with different absorbent properties. The intake and shaping layers can have selected configurations of absorbent capacities, densities, basis weights and/or configurations of sizes which are selectively constructed and arranged to provide desired combinations of liquid intake time, absorbent saturation capacity, absorbent retention capacity, z-directional liquid distribution along the thickness dimension of the article, shape maintenance, and aesthetics.

The shaping layer 36 can provide a desired, absorbent retention function and can provide operative levels of liquid storage and product shaping. The shaping layer can also be distinctively configured to provide a controlled deformation which can help the article to more effectively conform to the contours of the wearer's body during ordinary use. Additionally, the shaping layer can help provide an improved resistance to bunching and twisting.

The shaping layer may include natural fibers, synthetic fibers, superabsorbent materials, a woven fabric; a non-woven fabric; a coform web; a wet-laid fibrous web; a substantially unbonded airlaid fibrous web; an operatively bonded, stabilized-airlaid fibrous web; or the like, as well as combinations thereof. Additionally, the shaping layer can include a selected quantity of superabsorbent materials. In a particular aspect, the fibrous material of the shaping layer can be substantially free of debonding agents. In other aspects, the fibrous shaping layer may include a friction-reducing material, which can help increase the flexibility of desired sections of the article. The shaping layer may also include one or more components that can modify menses or inter-menstrual liquids In a particular arrangement, for example, the shaping layer 36 can include a fibrous, non-debonded, southern pine kraft woodpulp (e.g. NB 416), which is available from Weyerhaeuser, a business having offices located in Federal Way, Wash., U.S.A. In another arrangement, the shaping layer can include a fibrous woodpulp treated with an agent that helps enable densification and helps reduce stiffness (e.g. ND 416; which is also available from Weyerhaeuser).

In another arrangement, the shaping layer 36 can include a thermally-bonded, stabilized airlaid fibrous web available from Concert Fabrication (Concert code 225.1021), a business having offices located in Gatineaux, Quebec, Canada (e.g. Concert code 225.1021). The shaping layer 36 may optionally be provided by a similar, stabilized airlaid fibrous web available from Buckeye Technologies, Inc., a business having offices located in Memphis, Tenn., U.S.A.

In particular aspects for regular capacity and "long-maxi" articles, the shaping layer 36 can have an average basis weight which is at least a minimum of about 150 g/m². The shaping layer basis weight can alternatively be at least about 300 g/m², and can optionally be at least about 350 g/m² to provide improved performance. In other aspects, the shaping layer basis weight can be up to a maximum of about 700 g/m², or more. The shaping layer basis weight can alternatively be up to about 600 g/m², and can optionally be up to about 550 g/m² to provide improved effectiveness.

For high capacity and overnight products the shaping layer 36 can have an average basis weight which is at least a minimum of about 400 g/m². The shaping layer basis weight can alternatively be at least about 500 g/m², and can optionally be at least about 600 g/m² to provide improved performance. In other aspects, the shaping layer basis weight can be up to a maximum of about 1000 g/m², or more. The shaping layer basis weight can alternatively be up to about 900 g/m², and can optionally be up to about 800 g/m² to provide improved performance.

The pad shaping layer 36 can be configured to have a higher proportion of its absorbent material concentrated at or near the center of the article. This can provide increased absorbent capacity in the target intake area, while maintaining a relatively low average basis weight and a relatively high flexibility along the periphery of the shaping layer. The ratio of the center basis weight to the edge or end basis weights can be within the range of about 1.05–2.0. The basis weight ratio can alternatively be within the range of 1.1–1.5, and can optionally be within the range of about 1.2–1.3 to provide improved performance.

In other aspects, the shaping layer 36 can have an average density which is at least a minimum of about 0.05 g/cm³. The shaping layer density can alternatively be at least about 0.06 g/cm³ to provide improved performance. In other aspects, the shaping layer density can be up to a maximum of about 0.2 g/cm³, or more. The shaping layer density can alternatively be up to about 0.15 g/cm³, and can optionally be up to about 0.09 g/cm³ to provide improved effectiveness.

The shaping layer 36 can be also be configured such that the center of the shaping layer is relatively denser than the ends or edges. This can provide an improved density gradient within the shaping layer itself, and can provide an improved density gradient between the intake and shaping layers. Benefits are reduced side leakage, increased longitudinal fluid wicking, and improved surface dryness. The ratio of the center density to the edge or end densities can be within the range of about 1.05–2. The density ratio can alternatively be within the range of about 1.3–1.9, and can optionally be within the range of about 1.4–1.8 to provide improved performance.

Additionally, the shaping layer 36 can have a specific, absorbent saturation capacity which is at least a minimum of about 1 gram menses simulant per gram of shaping layer material (1 g/g). The specific saturation capacity of the shaping layer can alternatively be at least about 5 g/g, and can optionally be at least about 10 g/g to provide improved performance. In other aspects, the specific saturation capacity of the shaping layer can be up to a maximum of about 30 g/g, or more. The specific saturation capacity of the shaping layer can alternatively be up to about 25 g/g, and can optionally be up to about 20 g/g to provide improved effectiveness. In a desired arrangement, the specific absorbent saturation capacity of the shaping layer can be about 13 g/g, or can be about 15 g/g when the shaping layer includes a targeted 15% by weight add-on of particulate superabsorbent.

In a further feature, the shaping layer 36 can have a total, absorbent saturation capacity which is at least a minimum of about 5 grams of menses simulant (5 g). The total saturation capacity of the shaping layer can alternatively be at least about 20 g, and can optionally be at least about 30 g to provide improved performance. In other aspects, the total saturation capacity of the shaping layer can be up to a maximum of about 200 g, or more. The total saturation capacity of the shaping layer can alternatively be up to about 180 g, and can optionally be up to about 150 g to provide improved effectiveness. In a desired arrangement, the total saturation capacity of the shaping layer can be about 90 grams of menses simulant, or can be about 105 g when the shaping layer includes a targeted 15% by weight add-on of particulate superabsorbent.

The supplemental intake layer 32 can help desorb liquid from the cover 26, and can help manage surges or gushes of liquid entering the article. The intake layer can also help wick or otherwise distribute liquids through the absorbent structure. In desired arrangements, the intake layer can provide a temporary storage of liquid, and may provide a selected level of liquid retention. As representatively shown, the intake layer 32 can be operatively joined to the article and sandwiched between the cover 26 and the shaping layer 36.

The intake layer 32 or other supplemental layer may include natural fibers, synthetic fibers, superabsorbent materials, a woven fabric; a nonwoven fabric; a wet-laid fibrous web; a substantially unbonded airlaid fibrous web; an operatively bonded, stabilized-airlaid fibrous web; or the like, as well as combinations thereof. Additionally, the intake layer may include a selected quantity of superabsorbent materials, as desired. In a particular aspect, the fibrous material of the intake layer can be substantially free of debonding agents. The intake layer may also include one or more components that can modify menses or inter-menstrual liquid. In a particular arrangement, the intake layer 32 can be composed of a thermally-bonded, stabilized-airlaid fibrous web (e.g. Concert product code DT200.100.D0001), which is available from Concert Industries, a business having offices located in Gatineaux, Quebec, Canada.

In a desired feature, the intake layer 32 can have a relatively lower basis weight, as compared to the bottom, retention/shaping layer 36. Optionally, the basis weight of the intake layer may be equal or similar to the basis weight of the shaping layer. In another feature, the intake layer 32 can have a lower density (e.g., be more lofty), as compared to the retention/shaping layer 36. If the basis weight and/or density difference is sufficient, improved fluid partitioning in the retention layer can be provided. An additional hydrophilic gradient may be achieved if fibers of the intake layer are configured to be more "hydrophobic" than the fibers of the retention/shaping layer due to the inclusion of debonding agents and/or polymer binders in the intake layer structure.

In particular aspects, the intake layer 32 can have a basis weight which is at least a minimum of about 30 g/m². The intake layer basis weight can alternatively be at least about 100 g/m², and can optionally be at least about 150 g/m² to provide improved performance. In other aspects, the intake layer basis weight can be up to a maximum of about 250 g/m², or more. The intake layer basis weight can alternatively be up to about 225 g/m², and can optionally be up to about 200 g/m² to provide improved performance.

If the basis weight of the intake layer 32 is outside the desired values, the article can be too thick and bulky, and can provide poor comfort and excessive awareness of the article during use. An overly high basis weight can excessively decrease the amount of liquid transferred to the shaping layer 36, can undesirably increase the amount of liquid held in the intake layer and/or can be excessively expensive. An overly low basis weight can excessively limit the ability to acquire, temporarily store and transfer liquid, and can permit premature leakage. If the basis weight of the intake layer is outside the desired values, the article can also exhibit an excessively high rewet or flowback to the wearer's skin and provide an undesired wet, moist feel to the wearer. Additionally, the intake layer can present an excessively low void volume to subsequent inputs of liquid, and the low void volume can contribute to premature leakage and excessive rewet or flowback to the wearer's skin.

In other aspects, the intake layer 32 can have a density which is at least a minimum of about 0.01 g/cm³. The intake layer density can alternatively be at least about 0.02 g/cm³, and can optionally be at least about 0.04 g/cm³ to provide improved performance. In other aspects, the intake layer density can be up to a maximum of about 0.14 g/cm³, or more. The intake layer density can alternatively be up to about 0.10 g/cm³, and can optionally be up to about 0.08 g/cm³ to provide improved performance.

If the density of the intake layer 32 is outside the desired values, the article can exhibit excessive leakage, and can provide an undesired moist, wet feeling against the wearer's skin. An overly high density can limit the saturation capacity of the intake layer and can provide excessively low permeability. This can excessively slow the acquisition and intake of liquid. Additionally, an overly high density can decrease and inhibit the desired liquid transfer to the lower, shaping layer 36. Insufficient liquid transfer can increase rewet or flowback of liquid to the wearer's skin and can decrease the void volume in the intake layer that is available to absorb a follow-up input of liquid, resulting in an increased likelihood of a premature leak. An overly low density can provide an excessively low web tensile strength, and can cause web handling problems. Depending on the basis weight, a low density can provide an excessively thick bulky intake layer that can cause poor comfort and excessive awareness of the product. A low intake layer density can also allow discrete amounts of liquid to be immobilized within the intake structure. This liquid can then be available to increase the likelihood of liquid rewet and flowback to the wearer's skin. Additionally, an overly low density intake structure can provide excessively high permeability. As a result, the properties of liquid control, spreading, distribution and temporary storage can be inadequate. The article can also allow premature leakage or an undesirably moist, wet skin.

Additionally, the intake layer 32 can have a specific, absorbent saturation capacity which is at least a minimum of about 10 grams menses simulant per gram of intake layer material (10 g/g). The specific saturation capacity of the intake layer can alternatively be at least about 10.5 g/g, and can optionally be at least about 11 g/g to provide improved performance. In other aspects, the specific saturation capacity of the intake layer can be up to a maximum of about 15 g/g, or more. The specific saturation capacity of the intake layer can alternatively be up to about 14.5 g/g, and can optionally be up to about 14 g/g to provide improved effectiveness. In a desired arrangement, the specific saturation capacity of the intake layer can be about 13 g/g.

In a further feature, the intake layer 32 can have a total, absorbent saturation capacity which is at least a minimum of about 0.5 grams of menses simulant (0.5 g). The total saturation capacity of the intake layer can alternatively be at least about 5 g, and can optionally be at least about 10 g to provide improved performance. In other aspects, the total saturation capacity of the intake layer can be up to a maximum of about 23 g, or more. The total saturation capacity of the intake layer can alternatively be up to about 22 g, and can optionally be up to about 21 g to provide improved effectiveness. In a desired arrangement, the total absorbent saturation capacity of the intake layer can be about 17 grams of menses simulant.

The top, bodyside intake layer 32 of the present invention can be equal to or smaller in size, as compared to the size of the bottom, garment-side retention/pad shaping layer 36. For example, the intake layer 32 might have a surface area that is approximately 25–50% of the surface area of the shaping layer 36. The intake layer can desirably be substantially centered (in the longitudinal direction 22 and the cross-direction 24) with respect to the shaping layer, but may optionally be skewed or offset in a selected direction (e.g. along the longitudinal direction 22), depending on where the liquid is expected to first enter the absorbent article.

The top intake layer 32 may have any operative shape and/or design. For example, the intake layer may include a single piece of material, or multiple pieces of material, such as multiple strips of material. In addition, the intake layer 32 may include holes or apertures to better provide desired liquid-intake properties. The apertures may extend partially or completely through the z-directional thickness of the intake layer 32, as desired.

The amount of superabsorbent material in a selected layer or other component (e.g., the shaping layer 36) can be at least a minimum of about 1 wt %. The amount of superabsorbent material can alternatively be at least about 5 wt %, and can optionally be at least about 8 wt % to provide improved performance. In other aspects, the amount of superabsorbent material can be up to a maximum of about 75 wt %, or more. The amount of superabsorbent material can alternatively be up to about 35 wt %, and can optionally be up to about 20 wt % to provide improved effectiveness.

If the amount of superabsorbent is outside the desired values, there can be excessive leakage. If the amount of superabsorbent is too high, there can be a poor containment of the superabsorbent gel and an excessive amount of gel on the wearer's skin. Additionally, the transfer of liquid to the shaping layer may be inhibited or the product may have an inadequate rate of liquid intake, causing leakage and excessive wetness against the wearer's skin. The manufacturing costs can also become excessive.

The configuration of the embossment region or other stiffening region can help provide a controlled deformation which can allow the absorbent body and the article to more effectively conform to the contours of the wearer's body during ordinary use. The embossments can, for example, better channel and direct liquid away from the intake region of the article, and can more effectively move the liquid toward the article end portions 72. As a result, the article can more effectively present a drier cover surface to the wearer, and can provide improved fit and comfort.

In the embossment regions, the corresponding material or materials of the article are operatively compressed and substantially permanently deformed along the z-directional thickness dimension of the article. The corresponding material or materials in the embossment region are operatively molded to form a desired channel structure, and are substantially uncut.

By incorporating its distinctive features, the article can more effectively provide a desired controlled deformation of the absorbent structure, and can resist and control any pivoting or hinging action that may occur in the area that is affected by the embossment region. The embossed channels provided by the embossment region can effectively move liquid toward the end regions of the article, and the controlled hinging action can help provide an article shape or profile during use which can better conform to the wearer's body and be more comfortable. The embossment region can also improve the integrity of the absorbent body, can improve the attachment between any separately provided absorbent components, and can help reduce the undesired bunching and roping of the absorbent components.

The desired, increased stiffness region of the shaping layer can be provided by an embossment region which has been operatively stiffened by including a selected pattern or other array of embossments. More particularly, the first embossment array 40 can include a first base section 60 and a first complementary section 62, which include a plurality of embossment elements 44. The second embossment array 50 can include a second base section 64 and a second complementary section 66, which include a plurality of embossment elements 54. The sections of the embossment region can be formed in at least a portion of the absorbent shaping layer 36. Each base section 60, 64 is positioned laterally opposite to its corresponding complementary section 62, 66, respectively, on opposite sides of the longitudinal centerline 52. In a particular aspect, the pattern of embossment elements can provide a first, generally fishbone array 40 of embossment elements 44 positioned in a first, longitudinal half-portion of the shaping layer 36, and can provide at least a second, generally fishbone array 50 of embossment elements 54 positioned in a second, longitudinal half-portion of the shaping layer.

The first array 40 of embossment elements 44 can have a first, convergently arranged nose-end 70, and a first, relatively divergently arranged tail-end 74. In a like manner, the second array 50 of embossment elements 54 can have a second, convergently arranged nose-end 78, and a second, relatively divergently arranged tail-end 80. The first and second arrays of embossment elements can also be distinctively counter-positioned relative to each other. More particularly, the embossment array 40 can be arranged with its first nose-end 70 positioned toward a central region of the article 20, and its first tail-end 74 positioned toward the first end region 72 of the article 20. The second embossment array 50 can be counter-positioned by locating its second nose-end 78 toward the central region of the article, and locating its second tail-end 80 toward the second end region 72a of the article.

In an optional configuration, the first nose-end 70 can be positioned toward a first end region 72 of the article 20, and the first tail-end 74 can be positioned toward the central region of the article 20 (e.g. FIG. 10). Additionally, the second nose-end 78 can be positioned toward a second end region 72a of the article, and the second tail-end 80 can be positioned toward the central region of the article. In a desired feature, the embossment elements 44, 54 can be configured to substantially avoid intersecting in the medial section 38 of the absorbent body 30.

The first array 40 of stiffening elements (e.g. embossment elements 44) can be configured to provide a first base-side section 60 and a first complementary-side section 62. As representatively shown, the first complementary-side section can be located laterally opposite the first base-side section. Similarly, the second array 50 of stiffening elements (e.g. embossment elements 54) can be configured to provide a second base-side section 64 and a second complementary-side section 66. Additionally, the second complementary-side section can be located laterally opposite the second base-side section. As representatively shown, the arrangement of stiffening elements in the first complementary-side section 62 can be a substantially mirror image of the arrangement of stiffening elements in the first base-side section 60, and the arrangement of stiffening elements in the second complementary-side section 66 can be a substantially mirror image of the arrangement of stiffening elements in the second base-side section 64. Optionally, the embossment elements in a selected base-side section 60, 64 may be longitudinally offset by a discrete distance relative to the embossment elements in its corresponding complementary-side section 62, 66, respectively.

Figure 3:
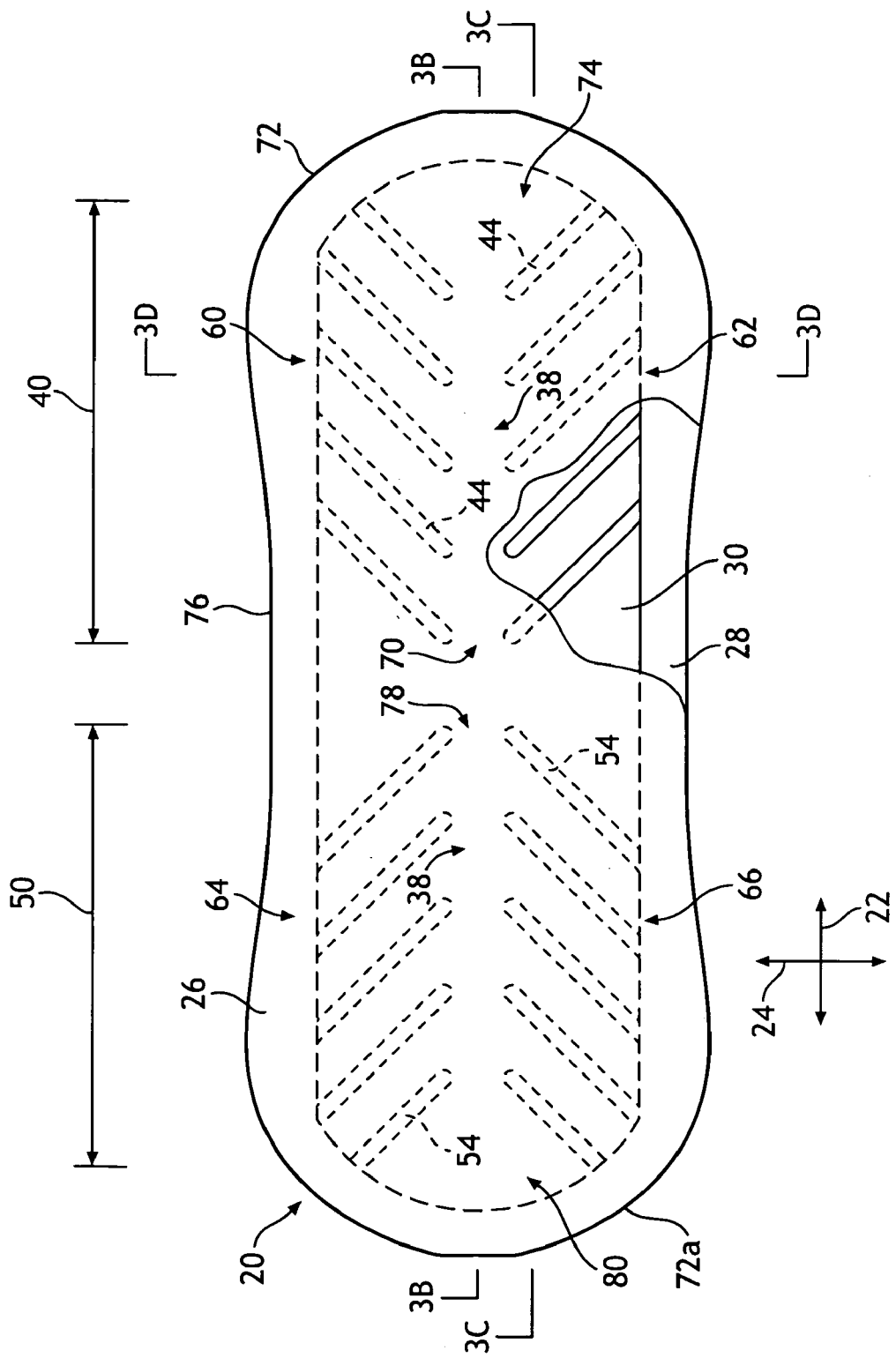
FIG. 3 shows a representative, partially cut-away, top plan view of a bodyside of an article having a deformation-control member which includes counter-positioned arrays of stiffening embossment elements.
Figure 3A:
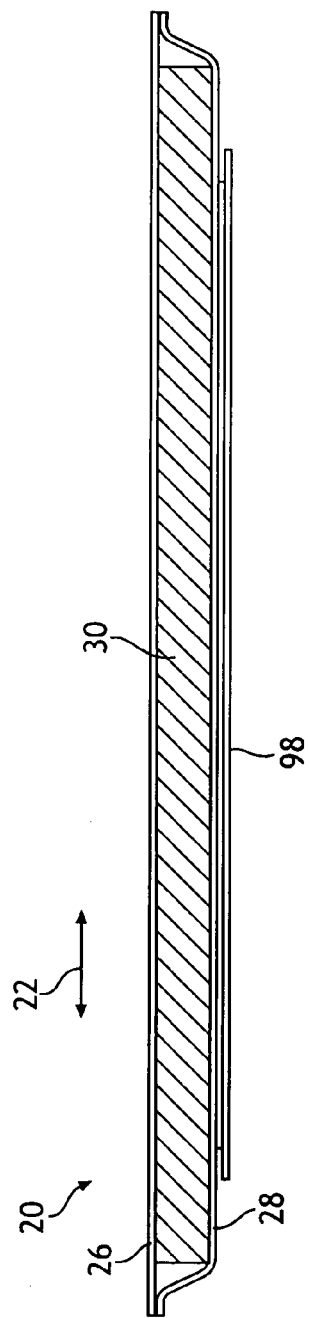
FIG. 3A shows a representative view of a longitudinal cross-section through a medial section of the article illustrated in FIG. 3.
Figure 3B:
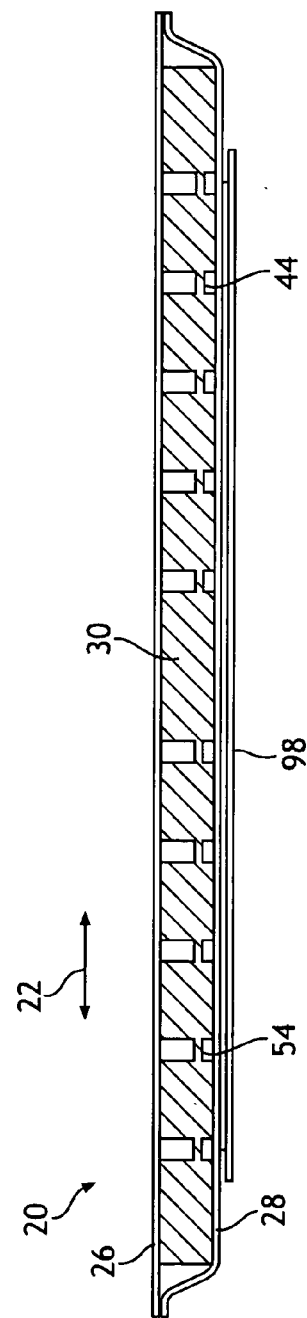
FIG. 3B shows a representative view of a longitudinal cross-section through an embossed section of the article illustrated in FIG. 3.
Figure 3C:
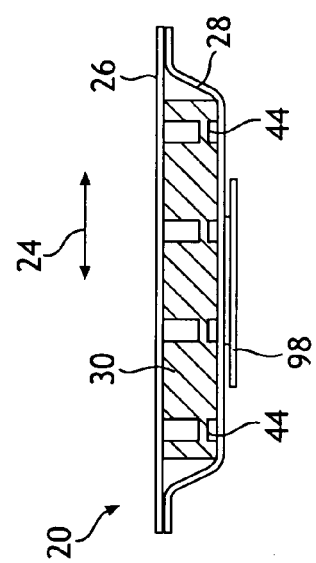
FIG. 3C shows a representative view of a transverse cross-section through the article illustrated in FIG. 3.
Figure 11:
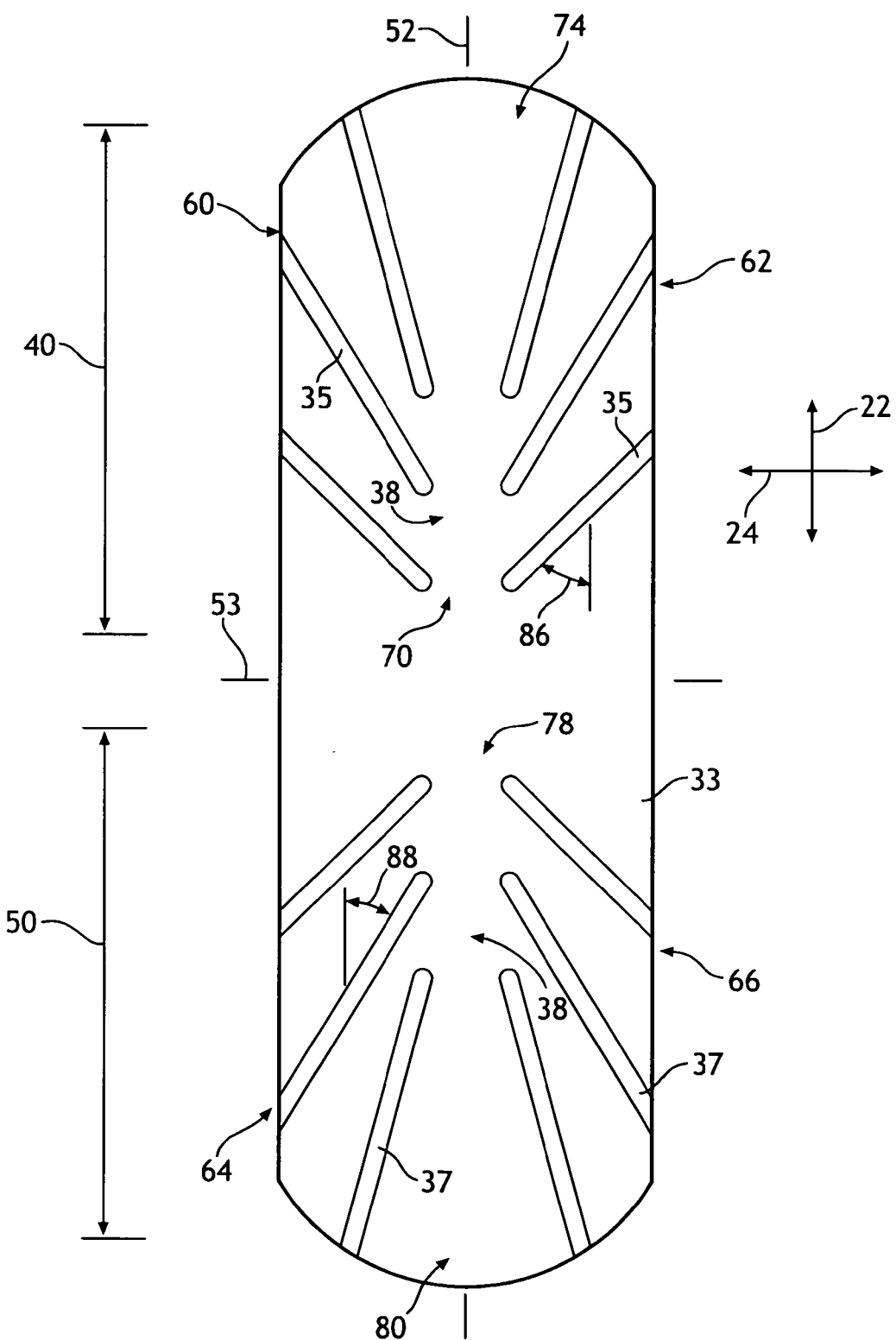
FIG. 11 shows a representative, top plan view of a deformation-control member which includes counter-positioned arrays of stiffening elements wherein the stiffening elements within an array have different alignment angles.
Figure 13:
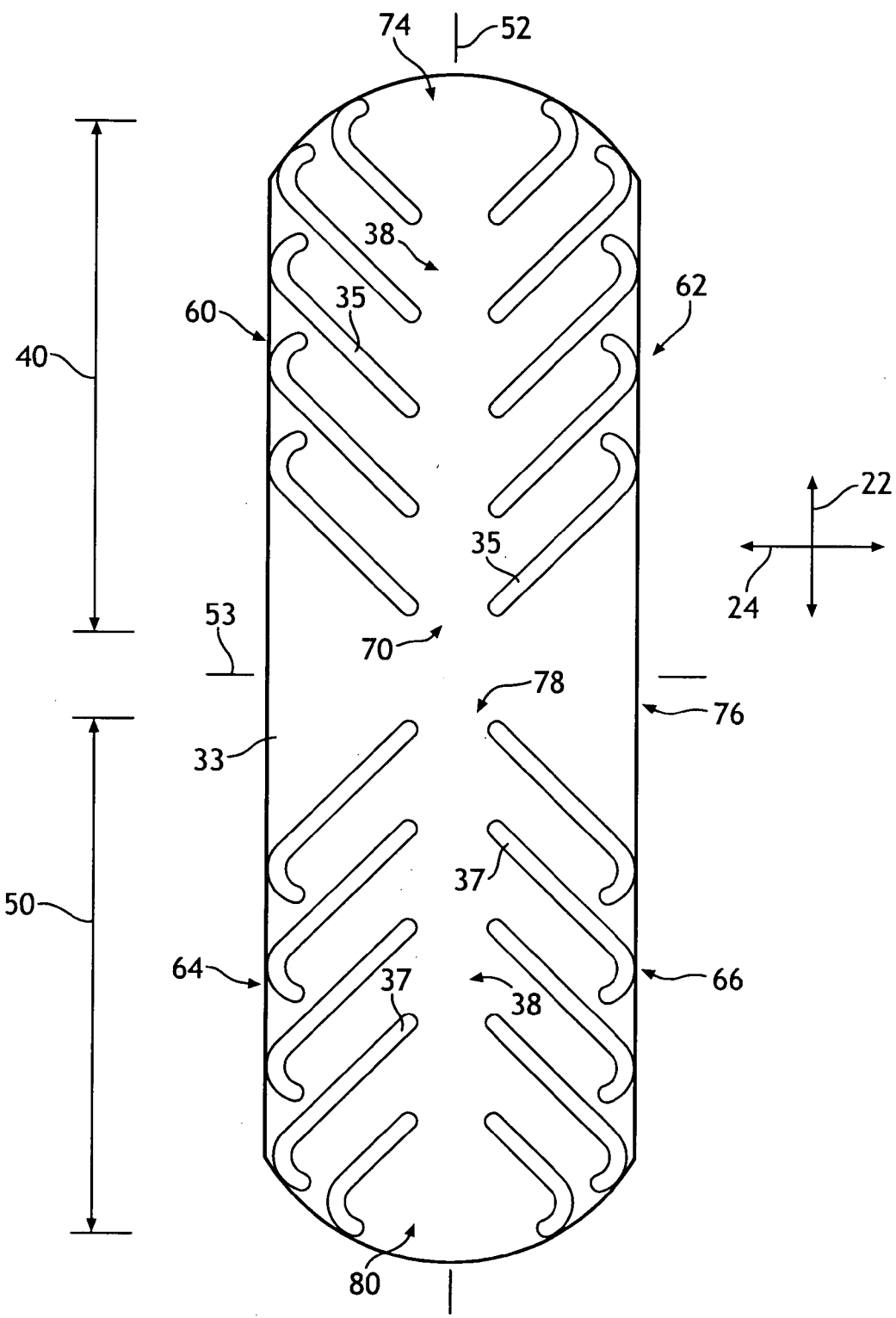
FIG. 13 shows a representative, top plan view of a deformation-control member which includes counter-positioned arrays of stiffening elements wherein at least a portion of the stiffening element is curvilinear.

Immediately adjacent, embossments elements 44 in the first base-side section 60 can be substantially parallel with each other along at least a major portion of their longitudinal length dimensions (e.g. FIGS. 1 and 3). Similarly, immediately adjacent embossment elements 54 in the second-base section 64 can be substantially parallel with each other along at least a major portion of their longitudinal length dimensions. In other configurations, selected portions of the immediately adjacent embossment elements can be nonparallel with each other (e.g. FIGS. 11 and 13).

With reference again to FIGS. 1, 3 and 6, the medial section 38 of the absorbent body 30 (or other deformation-control member) can be substantially non-embossed or otherwise non-stiffened. In a particular aspect, the medial section of at least the shaping layer 36 can be substantially non-stiffened (e.g. non-embossed). In other aspects, the medial section of any supplemental absorbent layers, such as intake layer 32, can also be substantially non-embossed and non-stiffened.

The medial section 38 can have an operative medial section width 56 and an operative medial section length 58. In particular aspects, the width 56 of the medial section can be at least a minimum of about 2 mm. The medial section width can alternatively be at least about 5 mm, and can optionally be at least about 10 mm to provide improved performance. In other aspects, the medial section width 56 can be up to a maximum of about 45 mm, or more. The medial section width can alternatively be up to about 25 mm, and can optionally be up to about 15 mm to provide improved effectiveness. The width of the medial section may be non-constant and variable, or may be substantially constant and substantially non-variable.

The length 58 of the medial section 38 can be at least a minimum of about 50 mm. The medial section length can alternatively be at least about 120 mm, and can optionally be at least about 150 mm to provide improved performance. In other aspects, the medial section length 58 can be up to a maximum of about 300 mm, or more. The medial section length can alternatively be up to about 200 mm, and can optionally be up to about 180 mm to provide improved effectiveness. The length of the medial section may be non-constant and variable, or may be substantially constant and substantially non-variable.

If the length and/or width dimensions of the medial section are outside the desired values, the article can exhibit poor shaping during use. Additionally, the article can cause excessive discomfort and exhibit poor leakage control.

Generally stated, the boundaries of the medial section can be observed by taking each immediately-adjacent pair of the individual stiffening elements (e.g. embossments 44, 54) within a base-section or complementary-section of an array of stiffening elements, and establishing a straight line that tangentially intercepts the inboard terminal end region on both of the immediately-adjacent pair of stiffening elements. The resulting series of tangential-intercept lines can then substantially outline the outer perimeter of the medial section.

Figure 9:
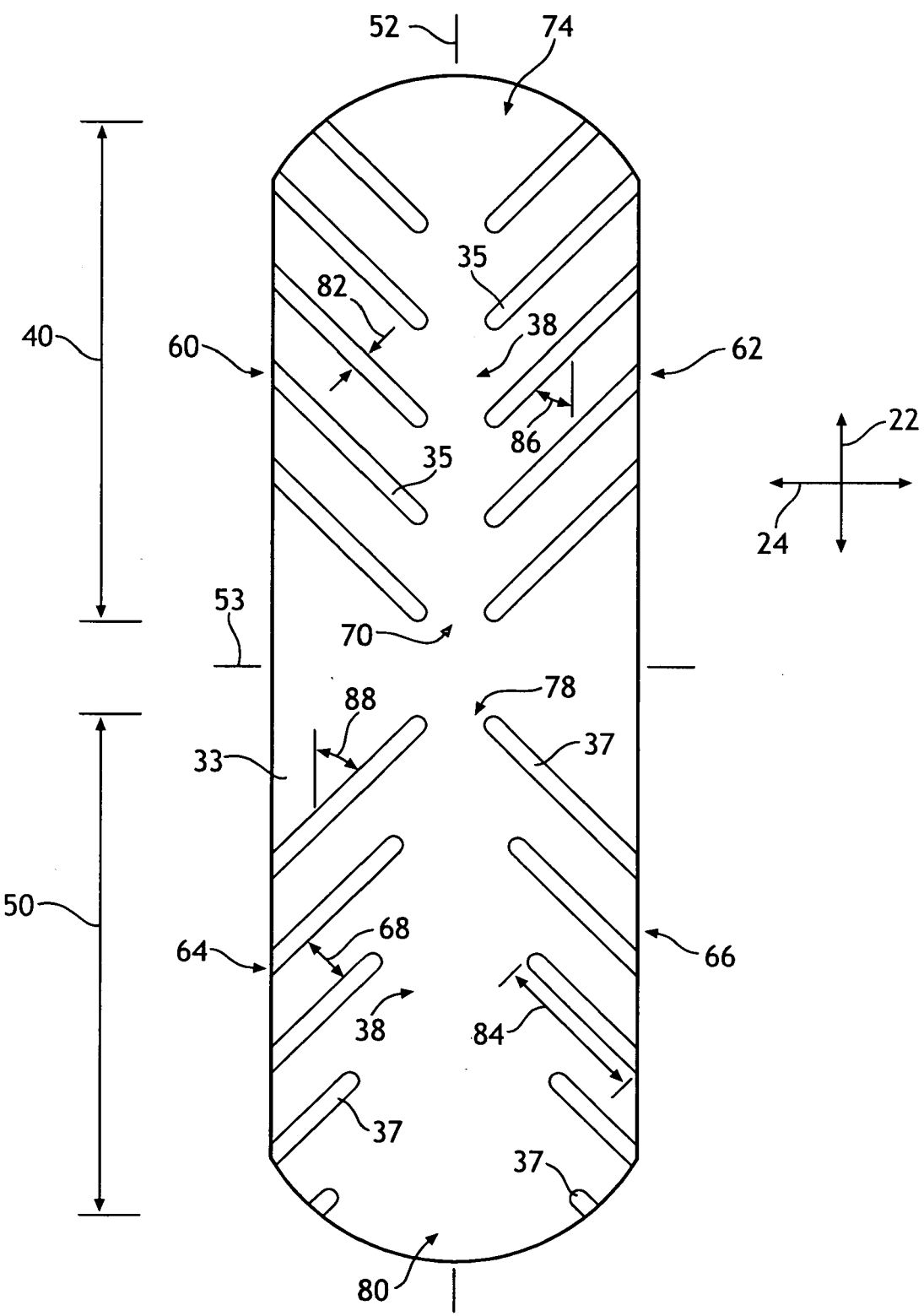
FIG. 9 shows a representative, top plan view of a deformation-control member which includes stiffening elements of differing length.

As representatively shown, the lateral side boundaries of the selected medial section 38 can be substantially parallel to the longitudinal centerline 52 of the article. Alternatively the lateral side boundaries of the selected medial section can be substantially non-parallel to the article longitudinal centerline 52. In a particular arrangement, the lateral side boundaries of the selected medial section can significantly diverge as the side boundaries extend from transverse centerline 53 toward a longitudinal end of the article (e.g. FIG. 9). In an optional arrangement, the lateral side boundaries of the selected medial section may significantly converge as the side boundaries extend from transverse centerline 53 toward a longitudinal end of the article.

In the selected stiffened region (e.g. the region having the pattern of embossments), the first stiffness array 40 can include at least a minimum of about 4 individual, separately-spaced, stiffening elements (e.g. the representatively shown embossment elements 44) which can adjust the flexibility of the corresponding region of the article. Additionally, the second stiffness array 50 can include at least a minimum of about 4 individual, separated spaced, stiffening elements (e.g. the representatively shown embossment elements 54) which can adjust the flexibility of the corresponding region of the article. Each stiffness array 40 and/or 50 can alternatively include at least about 10 individual stiffening elements (e.g. embossment elements), and can optionally include up to about 40 individual stiffening elements, or more, to provide improved performance.

If the number of individual, embossment or other stiffening elements is outside the desired values, the article can exhibit poorly controlled bending and reduced absorbent capacity. Additionally, the article can exhibit excessive stiffness and excessive leakage.

The individual embossment elements 44 and 54 or other stiffening elements can have a relatively smaller element-width dimension 82 and a relatively longer, element-length dimension 84. In particular aspects, the element-width dimension 82 can be at least a minimum of about 0.5 mm. The element-width can alternatively be at least about 2 mm, and can optionally be at least about 2.5 mm to provide improved performance. In other aspects, the element-width can be up to a maximum of about 20 mm, or more. The element-width can alternatively be up to about 12 mm, and can optionally be up to about 9 mm or 7 mm. In other desired arrangements, the element-width can be up to about 5 mm or 3.5 mm to provide improved effectiveness. It should be readily appreciated that the individual stiffening elements may have different element-widths or may have substantially the same element-width, as desired.

In further aspects, the element-length 84 can be at least a minimum of about 10 mm. The element-length can alternatively be at least about 15 mm, and can optionally be at least about 20 mm to provide improved performance. In still other aspects, the element-length can be up to a maximum of about 70 mm, or more. The element-length can alternatively be up to about 50 mm, and can optionally be up to about 30 mm to provide improved effectiveness. It should be readily appreciated that the individual stiffening elements may have different element-lengths or may have substantially the same element-length, as desired.

If the element-width and/or element-length dimensions of the embossment elements are outside the desired values, the article can exhibit poor bending control and reduced absorbent capacity. Additionally, the article can exhibit excessive stiffness and excessive leakage.

Figure 7:
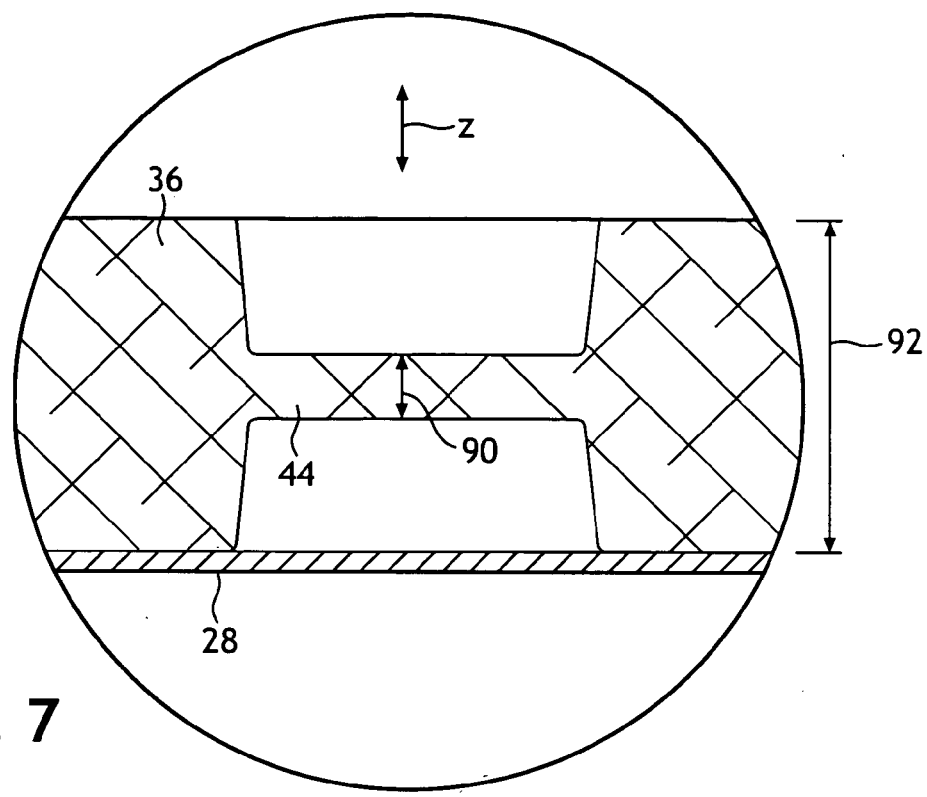
FIG. 7 shows an enlarged view of representative embossment element in which the material of the embossment is positioned at approximately a middle region of the thickness of the deformation-control member.
Figure 7A:
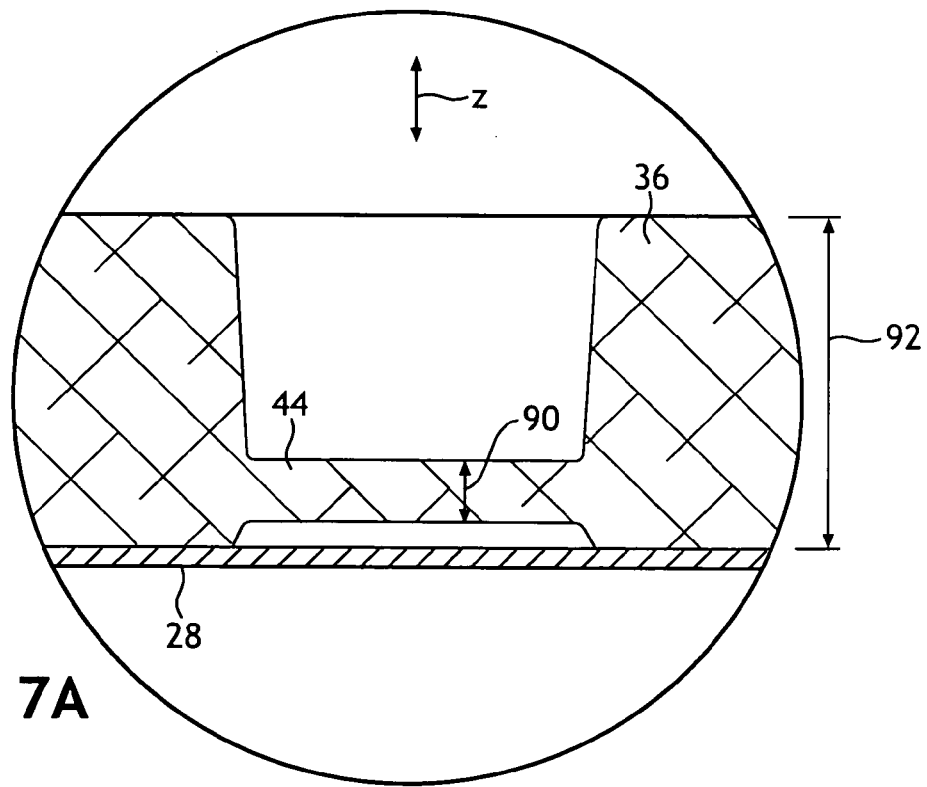
FIG. 7A shows an enlarged view of representative embossment element in which the material of the embossment element is offset along the thickness of the deformation-control member at a location that is relatively closer a backsheet layer.
Figure 7B:
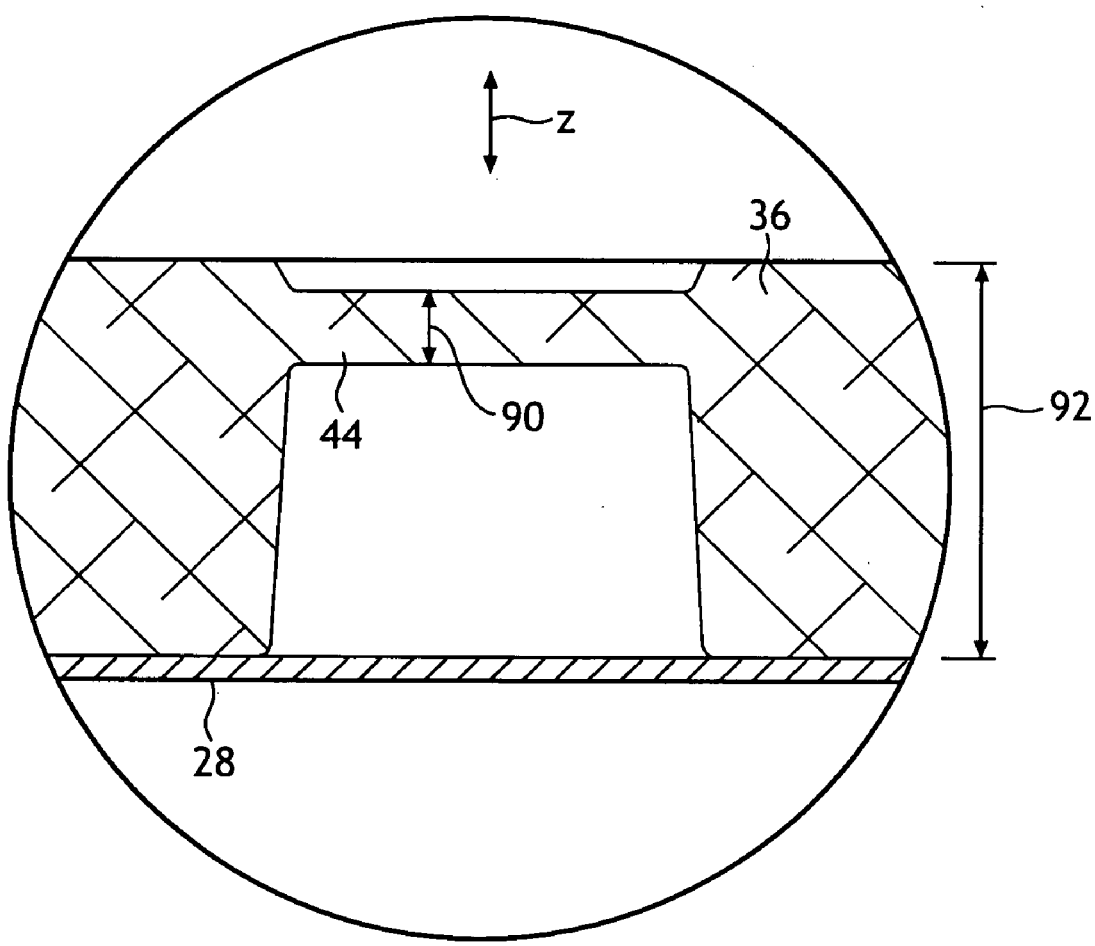
FIG. 7B shows an enlarged view of representative embossment element in which the material of the embossment element is offset along the thickness of the deformation-control member at a location that is relatively farther from a backsheet layer.

With reference to FIGS. 7 through 7B, the embossment elements or other stiffening elements can have a formed depth, and the embossment depth can provide for a selected caliper ratio or caliper percentage. In a particular feature, the embossment elements 44 and/or 54 can have an embossment caliper 90 which is a relatively small percentage of a substantially unembossed caliper 92 of the article. In a particular aspect, the caliper of the embossment element can be at least a minimum of about 25% of the caliper of the substantially unembossed region of the deformation-control member of the article. The embossment caliper can alternatively be at least about 50% of the caliper of the central region, and can optionally be at least about 60% of the substantially unembossed caliper to provide improved performance. In other aspects, the embossment caliper can be up to a maximum of about 95% of the caliper of the unembossed region of the deformation-control member, or more. The embossment caliper can alternatively be up to about 90% of the caliper of the unembossed region, and can optionally be up to about 75% of the unembossed caliper to provide improved effectiveness.

Where a component layer (e.g. the shaping layer 36) provides the deformation-control member, the central caliper is determined at the largest caliper, unembossed section of the component layer (e.g. shaping layer 36) that is found within the article medial section 38. The embossment caliper percentage is determined by the following formula:

Embossment caliper percentage=100\*(embossment caliper÷unembossed caliper).

The caliper measurements should include only the material of the deformation-control layer.

The stiffening element can be selectively positioned along the z-directional thickness dimension of the deformation-control layer. In a particular aspect of the invention, the stiffening element (e.g. the region of embossed material 44) can be located at approximately the middle of the thickness of the deformation-control member (e.g. shaping layer 36), as representatively shown in FIG. 7. In another aspect, stiffening element can be positioned away from the middle of the thickness dimension and offset away from the bodyside of the article (e.g. relatively closer to the backsheet or baffle 28) as representatively shown in FIG. 7A. As a result, when laterally inwardly-directed compressive forces are applied, the lateral sides of the article can tend to bend upwardly (concave toward the bodyside of the article) to provide selected absorbency advantages. A further aspect of the invention can have the stiffening element positioned away from the middle of the thickness dimension and offset toward the bodyside of the article (e.g. relatively farther away from the backsheet or baffle 28,) as representatively shown in FIG. 7B. As a result, when laterally inwardly-directed compressive forces are applied, the lateral sides of the article can tend to bend downwardly (convex toward the bodyside of the article) to provide particular fit advantages.

The caliper measurements and the relative positions of the stiffening elements can be optically determined from product cross-sections. A suitable measuring system can employ a QUANTIMET 600 Image Analysis System (available from Leica, Inc., a business having offices located in Cambridge, United Kingdom) equipped with QWIN version 1.06A software. A substantially equivalent measuring system may optionally be employed. Transverse cross-sections of the product can be created by cryogenically freezing the article with liquid nitrogen, and transversely cutting the frozen article into sections 1 cm wide (width measured along the longitudinal direction 22). A suitable cutting device is a BERKEL Commercial Food Processing Machine—Model#909, which is available from Berkel Incorporated, a business having offices located in LaPorte, Ind., U.S.A. Substantially equivalent cutting devices may optionally be employed.

If the caliper percentage is outside the desired values, the article may not provide a desired movement and distribution of liquid, and the article may not properly deform to match wearer's body contours.

A selected proportion of the embossment elements 44, 54 (or other stiffening elements) can be substantially linear. Alternatively, a selected proportion of the embossment elements 44, 54 can be substantially curvilinear. Optionally, each stiffening array 40, 50 can include a combination of linear and curvilinear embossment elements. In another aspect, at least a portion of each individual embossment element or other stiffening element can be substantially linear. Alternatively, a selected portion of each individual embossment element 44, 54 can be substantially curvilinear. Optionally, each individual embossment element can include a combination of linear and curvilinear portions (e.g. FIG. 13).

The individual embossment elements 44, 54 can be discontinuous or substantially continuous, as desired. In a desired configuration, at least a majority of the embossment elements can be substantially continuous along their length dimension.

Figure 14:
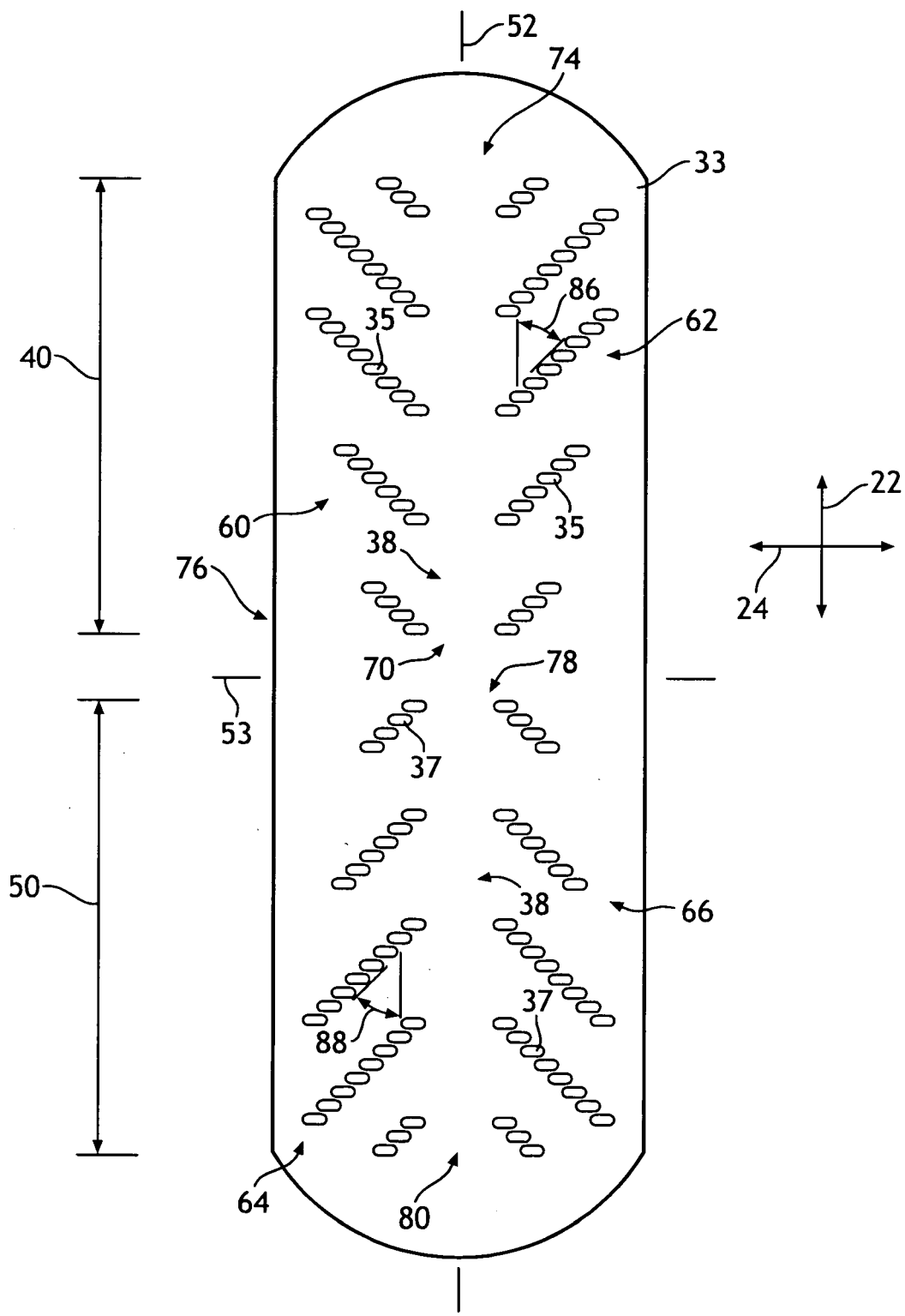
FIG. 14 shows a representative, top plan view of a deformation-control member which includes counter-positioned arrays of discontinuous stiffening elements.
Figure 14A:
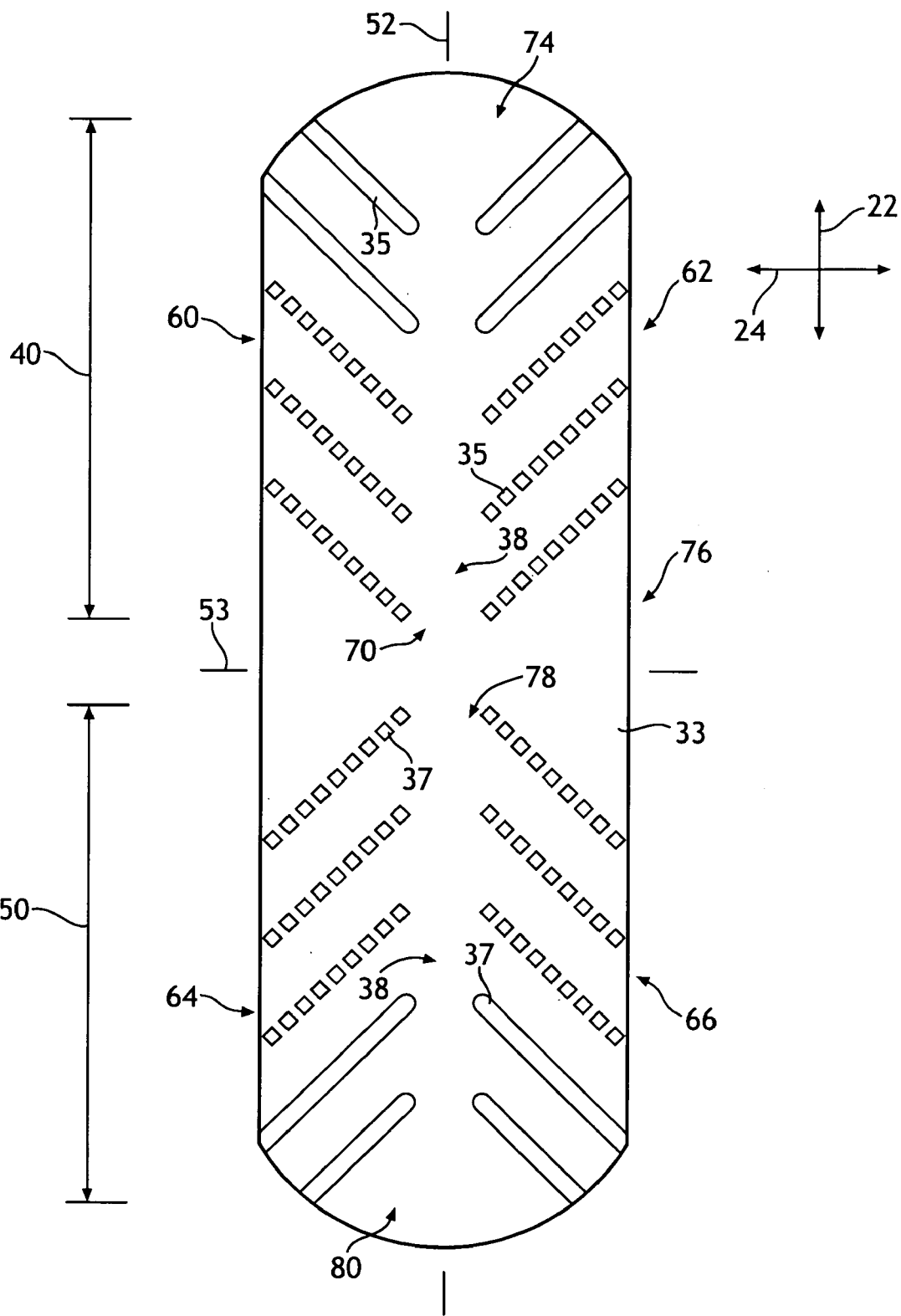
FIG. 14A shows a representative, top plan view of a deformation-control member which includes counter-positioned arrays having a combination of discontinuous stiffening elements and substantially continuous stiffening elements.
Figure 14B:
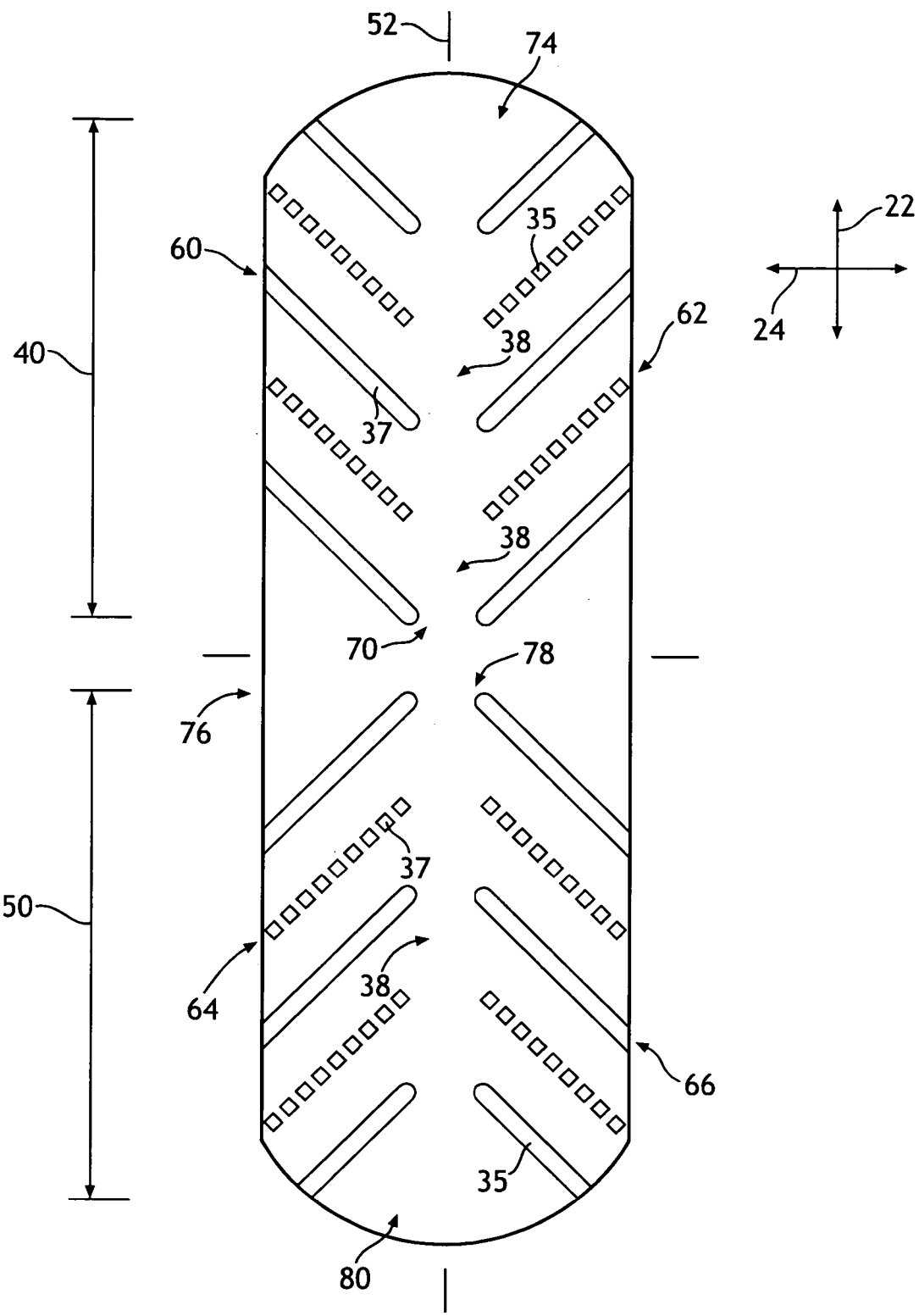
FIG. 14B shows a representative, top plan view of a deformation-control member which includes counter-positioned arrays having another combination of discontinuous stiffening elements and substantially continuous stiffening elements.

With reference to FIGS. 14 through 14B, at least some of the embossment elements can be discontinuous. In a desired aspect, the discontinuous embossment elements can be located and arranged with a selected pattern in the intermediate section 76 of the article 20. Alternatively, the discontinuous embossment elements can be intermingled or otherwise combined with continuous embossment elements in any desired pattern (e.g. FIGS. 14A and 14B).

In the various configurations of the invention, embossment elements or other stiffening elements 35 of the first array 40 can substantially avoid entering into an appointed medial section 38 of the absorbent body 30. Additionally, the embossment elements or other stiffening elements 37 of the second array 50 can substantially avoid entering into the medial section 38 of the absorbent body.

When the stiffening elements significantly enter into the medial section 38 of the absorbent body 30 or otherwise significantly intersect with one another, the article can exhibit a reduced ability to flex upwardly toward the body of the wearer along the medial section of the article, and a reduced ability to provide a desired shaping of the article during use. Additionally, the article can exhibit poor fit and poor absorbency with increased leakage.

Figure 12:
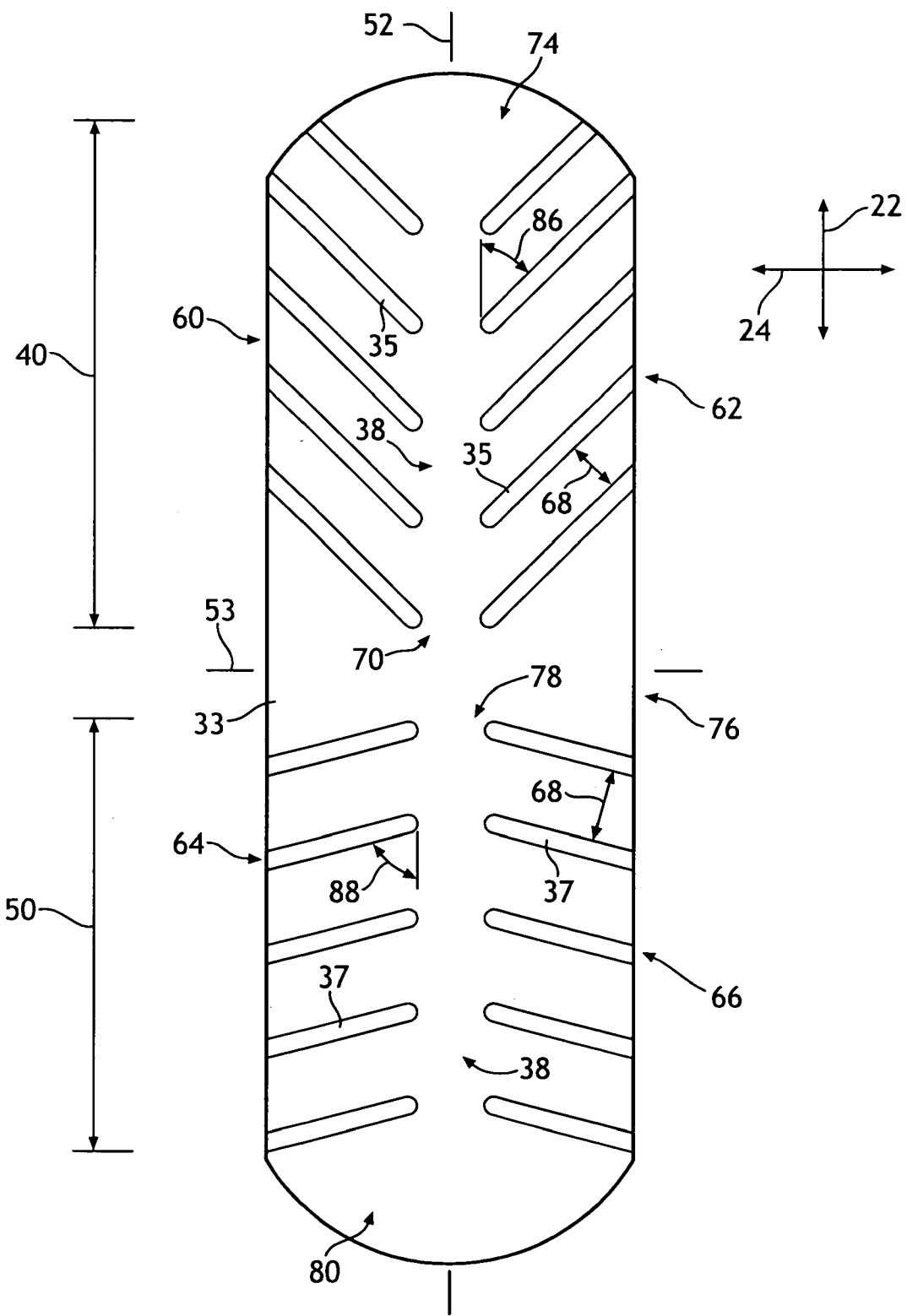
FIG. 12 shows a representative, top plan view of a deformation-control member which includes counter-positioned arrays of stiffening elements wherein the stiffening elements within the first and second arrays have different alignment angles.

With reference to FIGS. 1 and 12, the embossment elements or other stiffening elements (35, 37) can have a selected separation distance 68 between immediately adjacent embossment elements. In a particular aspect, the separation distance can be at least a minimum of about 0.5 mm. The separation distance can alternatively be at least about 5 mm, and can optionally be at least about 10 mm to provide improved performance. In other aspects, the separation distance 68 can be up to a maximum of about 40 mm, or more. The separation distance can alternatively be up to about 25 mm, and can optionally be up to about 14 mm to provide improved effectiveness. With respect to immediately adjacent stiffening elements, the separation distance 68 can be non-constant (e.g. FIG. 11) or substantially constant, as desired.

If the separation distance is outside the desired values, the article can be less able to provide a desired shaping of the article during use. Additionally, the article can exhibit poorer fit and poorer absorbency with increased leakage.

The first array 40 of stiffening elements (e.g. embossment elements 44) can be distinctively angled, and can have a first alignment angle 86 (e.g. FIGS. 1 and 10). In particular aspects, the first alignment angle 86 of the selected stiffening elements can be at least a minimum of about 15 degrees. The first alignment angle can alternatively be at least about 30 degrees, and can optionally be at least about 40 degrees to provide improved performance. In other aspects, the first alignment angle can be up to a maximum of about 75 degrees, or more. The first alignment angle can alternatively be up to about 60 degrees, and can optionally be up to about 50 degrees to provide improved effectiveness. The individual stiffening elements (e.g. embossment elements 44) can have different alignment angles 86 or may have substantially the same alignment angle, as desired.

The second array 50 of stiffening elements (e.g. embossment elements 54) can also be distinctively angled, and can have a second alignment angle 88. In particular aspects, the second alignment angle 88 of the selected stiffening elements can be at least a minimum of about 15 degrees. The second alignment angle can alternatively be at least about 30 degrees, and can optionally be at least about 40 degrees to provide improved performance. In other aspects, the second alignment angle can be up to a maximum of about 75 degrees, or more. The second alignment angle can alternatively be up to about 60 degrees, and can optionally be up to about 50 degrees to provide improved effectiveness. The individual stiffening elements (e.g. embossment elements 54) can have different alignment angles 88 or may have substantially the same alignment angle, as desired.

The alignment angles 86 and 88 are the acute angles measured from a line parallel to the longitudinal direction 22 to an element line that is parallel to the lengthwise centerline of the corresponding stiffening element (e.g. embossment element). The distinctive alignment angles of the stiffening elements can help the article provide a desired shaping of the article during use. In particular, the article can exhibit an improved ability to more consistently and more reliably flex upwardly toward the body of the wearer along the medial section of the article during ordinary use. Additionally, the article can more effectively provide a desired torsional stiffness, and can more effectively resist excessive twisting. Accordingly, the article can exhibit better fit and better absorbency with reduced leakage.

Figure 8:
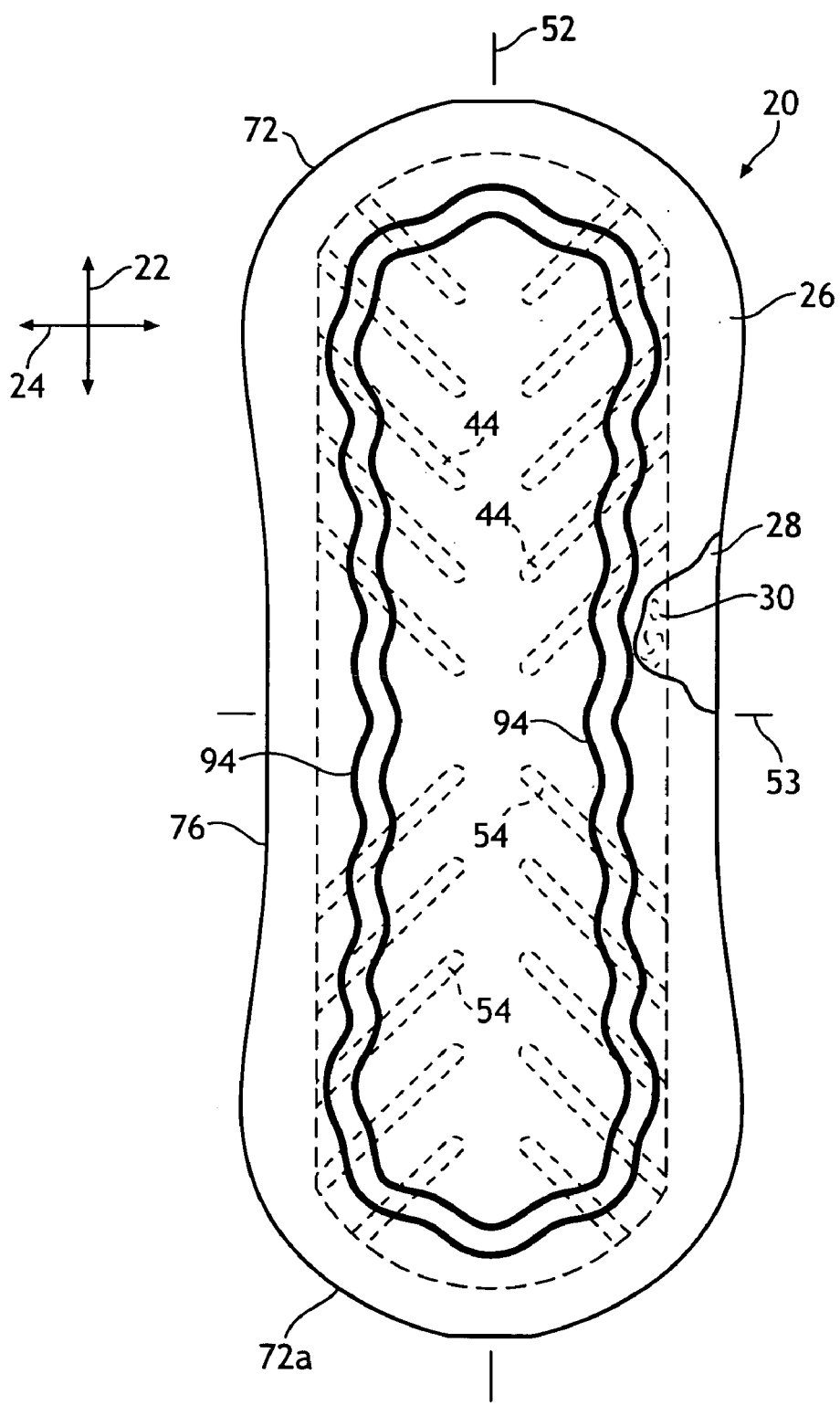
FIG. 8 shows a representative, partially cut-away, top plan view of a bodyside of an article having a perimeter embossment and a deformation-control member which includes counter-positioned arrays of stiffening elements.

With reference to FIG. 8, the absorbent body 30 (or other deformation-control member) can further include a perimeter embossment 94 which can be located proximally adjacent at least a portion of a terminal, perimeter edge of the absorbent body 30. The embossment elements 44, 54 may or may not intersect the perimeter embossment 94, as desired. The embossment elements 44 and/or 54 may, for example, include relatively outboard end sections which are curved or otherwise configured to substantially avoid intersecting the perimeter embossment 94.

In another aspect, the first complementary-side section 62 section can be laterally spaced-away from the first base-side section 60. Similarly, the second complementary-side section 66 can be laterally spaced-away from the second base-side section 64. As representatively shown, the spacing distance between the complementary-side section and its corresponding base-side section, can generally equal the width dimension of the medial section 38 of the absorbent body 30.

In optional arrangements, the article 20 may include additional components or component layers, as desired. For example, a transfer layer may be positioned between the intake layer 32 and the shaping layer 36. Additionally, a selected configuration (e.g. one or more strip regions) of a garment attachment mechanism (e.g. a garment-attachment adhesive 96) may be distributed onto the garment-side of the article to help secure the article to a wearer's undergarment. Typically, the garment adhesive is distributed over the garment-side of the baffle, and one or more layers or sheets of release material 98 are removably placed over the garment adhesive to cover the adhesive for storage prior to use (e.g. FIG. 15). Optionally, the garment attachment mechanism can include an operative component of a mechanical fastening system. For example, the garment attachment mechanism can include an operative component of a "hook-and-loop" type of fastening system.

In a particular feature, the garment attachment mechanism (e.g. garment adhesive 96) can be selectively distributed over one or more area-portions that substantially correspond to the location of the selected stiffness-control regions provided by the various base and complementary sections of the configured arrays of stiffening elements. With reference to FIG. 15A, for example, a selected portion of the garment attachment mechanism can be distributed over an area-portion having a size and shape that is substantially limited to and approximately matches the size and shape of the area occupied by its corresponding stiffness-control region. Additionally, the location (with respect to the longitudinal and transverse directions) of the area-portion of the garment attachment mechanism can approximately match the location of its corresponding stiffness-control region.

An alternative feature of the invention can have garment attachment mechanism configured to include a plurality of individual, garment attachment segments. Each individual segment of the garment attachment mechanism can be configured to approximately match the longitudinal-transverse location and the size of the area occupied by a corresponding stiffening element, as representatively shown in FIG. 15B. The selective distributions of the garment attachment mechanism can help assist the operability of the stiffening elements, and can help regulate the desired bending and shaping of the deformation-control member.

The article 20 can include a system of side-panel or wing portions 42. The side-panels can be unitarily formed from a selected component of the article, such as the cover and/or the baffle, and are integrally connected to appointed sections of the side regions along the intermediate portion 76 of the article. Alternatively, the side-panels or wings can be separately provided members that are subsequently attached or otherwise operatively joined to the intermediate portion of the article 20 (e.g. FIGS. 6 and 15).

The side-panels can have an appointed storage position in which the side-panels 42 are directed generally inwardly toward the longitudinally-extending centerline 52. As illustrated, the side-panel that is connected to one side margin may have sufficient cross-directional length to extend and continue past the centerline 52 to approach the laterally opposite side margin of the article. The storage position of the side-panels can ordinarily represent an arrangement observed when article is first removed from its wrapper or other packaging. Prior to placing the article into a bodyside of an undergarment prior to use, the side-panels 42 can be selectively arranged to extend laterally from the side regions of the article intermediate portion 76. After placing the article in the undergarment, the side-panels 42 can be operatively wrapped and secured around the side edges of the undergarment to help hold the article in place, in a manner well known in the art.

The side-panel portions 42 can have any operative construction, and can include a layer of any operative material. Additionally, each side-panel can comprise a composite material. For example, the side-panels may include a spunbond fabric material, a bi-component spunbond material, a necked spunbond material, a neck-stretched-bonded-laminate (NBL) material, a meltblown fabric material, a bonded carded web, a thermal bonded carded web, a through-air bonded carded web or the like, as well as combinations thereof.

Each side-panel 42 can be joined to its corresponding side region of the article in any operative manner. For example, the side-panel can be joined to the cover 26, the baffle 28 or another article component, as well as any combination thereof. In the illustrated example, each side-panel 42 is joined to the outward, garment-side surface of the baffle 28, but may optionally be joined to the bodyside surface of the baffle. The side-panel can be attached with hotmelt adhesive, but any other operative adhesive or attachment mechanism may alternatively be employed.

In another feature, each side-panel portion 42, or any desired combination of the employed side-panel portions, can include a panel-fastener component which is operatively joined to an appointed engagement surface of its associated side-panel. The panel-fastener can include a system of interengaging mechanical fasteners, a system of adhesive fasteners or the like, as well as combinations thereof.

Figure 15:
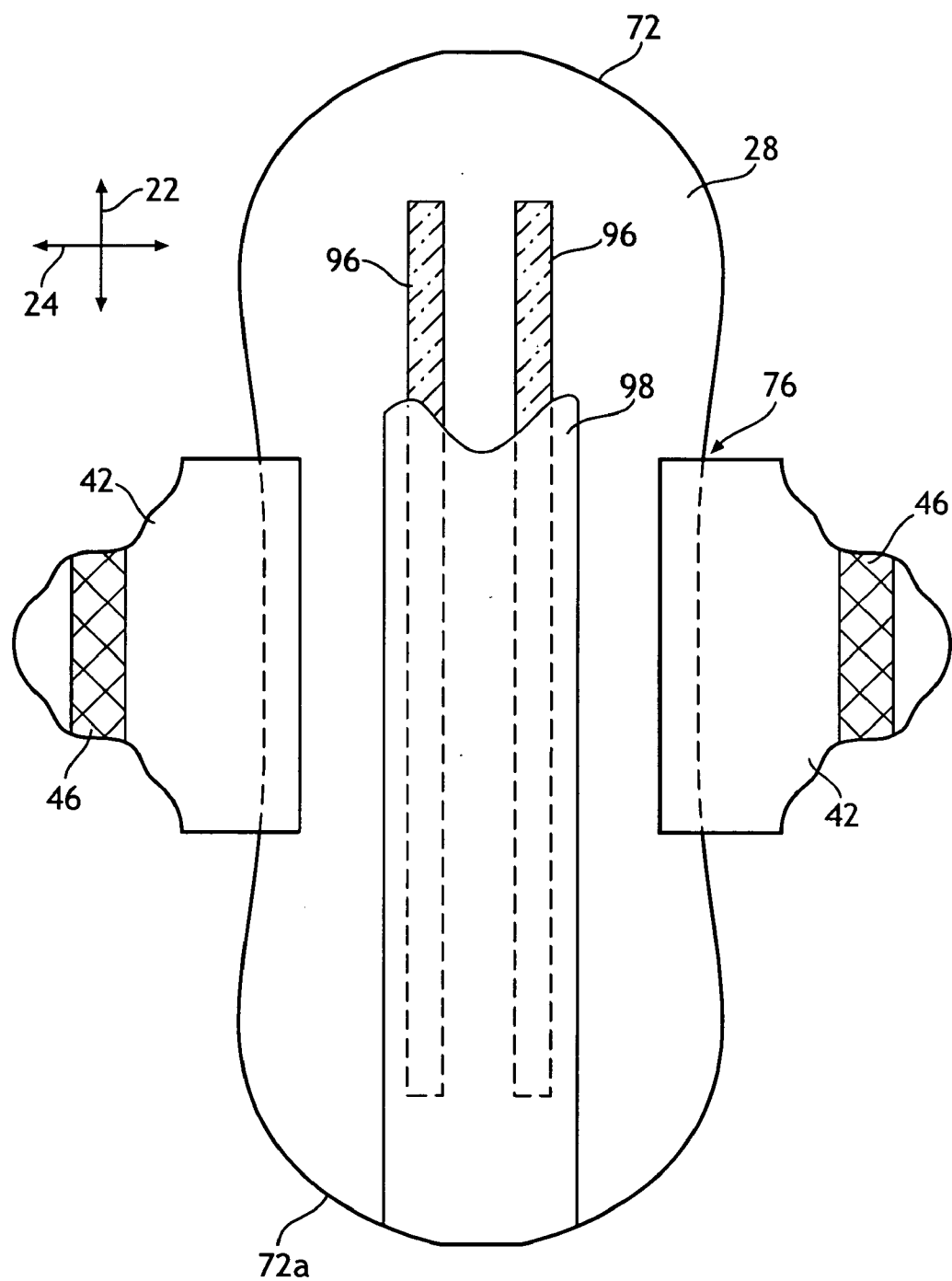
FIG. 15 shows a representative, partially cut-away, plan view of a garment-side of a feminine care article having side-panel portions.
Figure 15A:
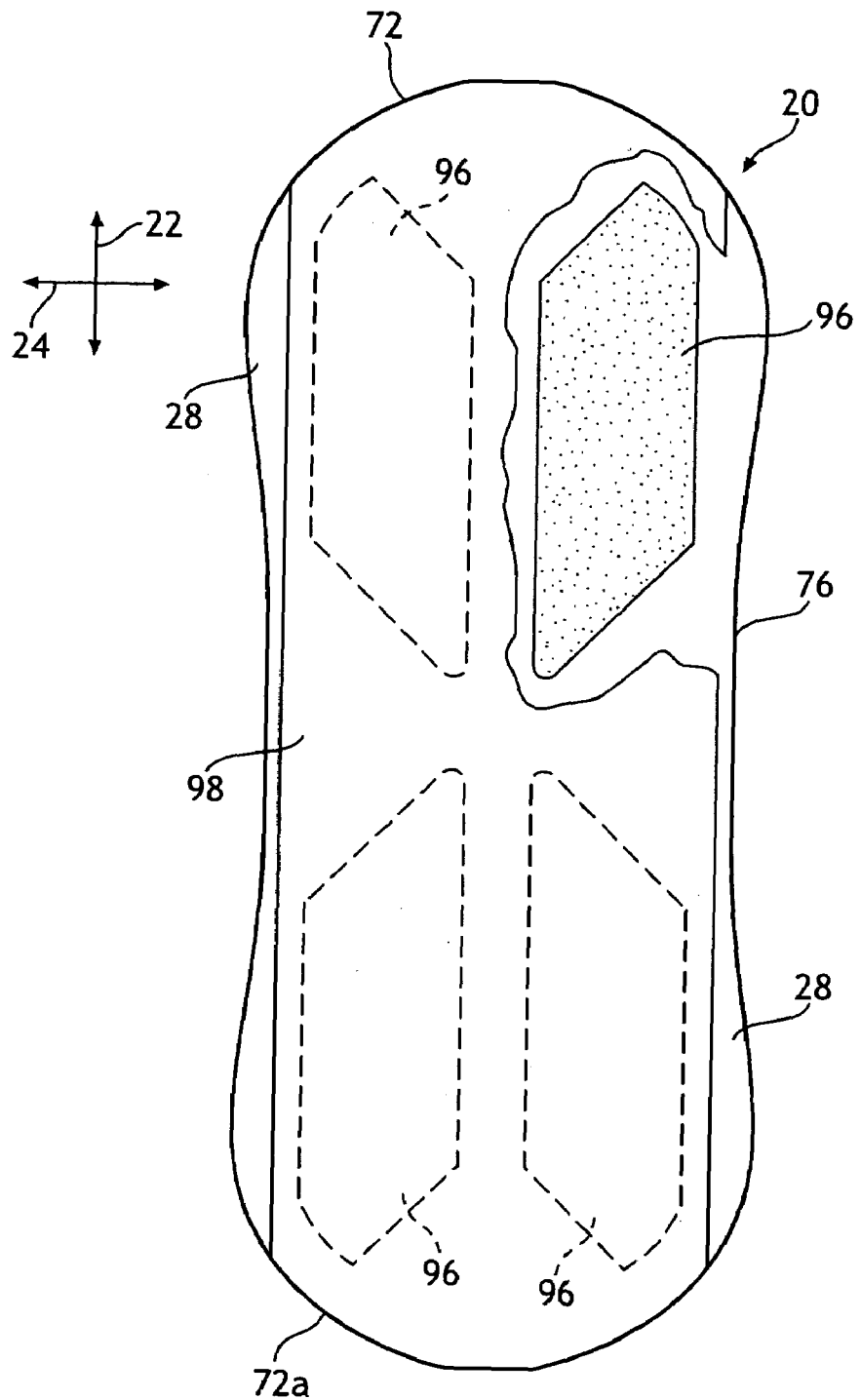
FIG. 15A shows a representative, partially cut-away, plan view of a garment-side of a feminine care article having a garment attachment mechanism arranged to substantially match the location of corresponding stiffening regions.
Figure 15B:
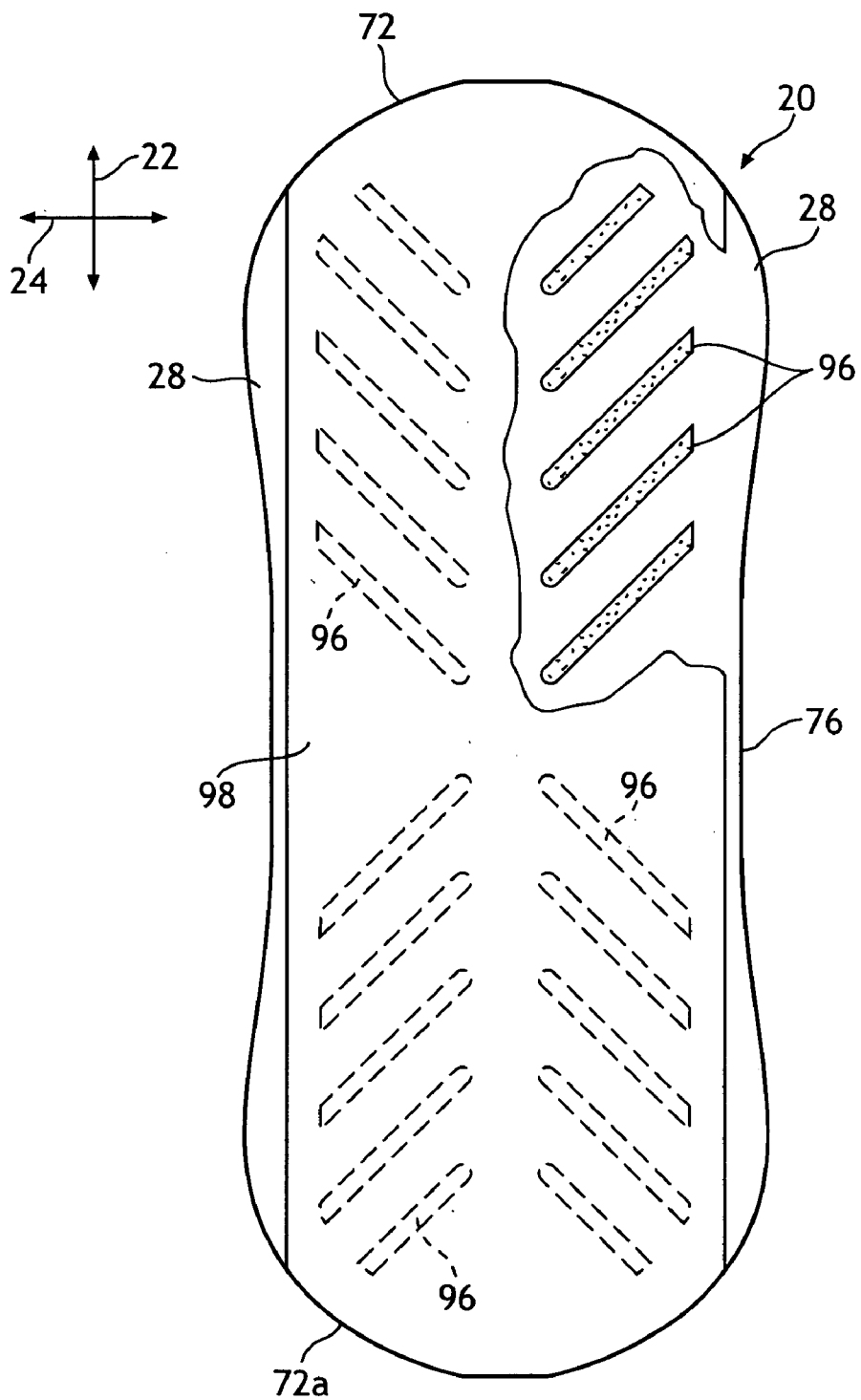
FIG. 15B shows a representative, partially cut-away, plan view of a garment-side of another feminine care article having a garment attachment mechanism arranged to substantially match the location of corresponding stiffening elements.

As representatively shown in FIGS. 6 and 15, for example, each side-panel 42 can include a cooperating component of an interengaging mechanical fastener system. As illustrated, the component can be a "male" component 46 (e.g. a hook component) of the fastener system. Any operative hook component may be employed. For example, a suitable hook component materials can include a J-hook, mushroom-head hook, flat-top nail-head hook, a palm-tree hook, a multiple-J hook or the like, as well as combinations thereof. Alternatively, either or both side-panels 42 can include a panel-fastener system which incorporates an operative adhesive. The adhesive may be a solvent-base adhesive, a hotmelt adhesive, a pressure-sensitive adhesive, or the like, as well as combinations thereof.

An operative first section of the selected hook component 46 can be joined to a major facing surface of at least a first side-panel portion 42, and can be configured to contact or otherwise engage a second side-panel portion during ordinary use. Additionally, an operative second section of a hook component, composed of the same or different type of hook material, can be joined to a major facing surface of the second side-panel portion, and can be configured to contact or otherwise engage an outward surface of the wearer's undergarment during ordinary use. For example, the hook component can be arranged to operatively engage and removably attach to the outward surface of a crotch region of the undergarment.

Each side-panel portion 42, or any desired combination of the employed side-panel portions, can include a loop or other "female" component 48 of an interengaging mechanical fastener system. Any operative loop component may be employed. For example, a suitable loop component material can include a woven fabric, a knit fabric, a nonwoven fabric, a fabric laminated to a substrate or the like, as well as combinations thereof.

An operative first section of a selected loop component 48 can be joined to a major facing surface of at least the second side-panel portion 42a, and can be configured to contact or otherwise engage the hook component 46 on the first side-panel portion 42 during ordinary use. Additionally, an operative second section of a loop component 48a, composed of the same or different type of loop material, can be joined to a major facing surface of the first side-panel portion 42. As a result, the user can have the option of alternatively attaching the second hook component 46a of the second side-panel onto the second loop component 48a of the first side-panel. Accordingly, the first hook component 46 may alternatively be engaged with the outward surface of the wearer's undergarment.

Each or any desired combination of the provided loop components 48 may be a separately provided member that is subsequently joined and assembled to its corresponding side-panel portion 42. In a desired feature, each or any desired combination of the provided loop components can be integrally provided by the material employed to construct its corresponding side-panel portion.

In the various arrangements of the present invention, the hook component 46 can be configured to have a particularly selected hook concentration or density (hooks per unit area). In a particular aspect, the hook density can be at least a minimum of about 1500 hooks/in$^2$ (about 232 hooks/cm$^2$). The hook density can alternatively be at least about 2000 hooks/in$^2$ (about 310 hooks/cm$^2$), and can optionally be at least about 3000 hooks/in$^2$ (about 465 hooks/cm$^2$) to provide improved performance. In another aspect, the hook density can be not more than a maximum of about 7000 hooks/in$^2$ (about 1085 hooks/cm$^2$). The hook density can alternatively be not more than about 6000 hooks/in$^2$ (about 930 hooks/cm$^2$), and can optionally be not more than about 5000 hooks/in$^2$ (about 775 hooks/cm$^2$) to provide improved performance.

Examples of suitable hook materials can include 85-Series and 61-Series hook materials available from Velcro, U.S.A., a business having offices located in Manchester, N.H., U.S.A. The hook materials can have a hook density of about 775 hooks/cm$^2$.

In a particular aspect, the material of the loop component 48 may include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. Pat. No. 5,858,515 entitled PATTERN-UNBONDED NONWOVEN WEB AND PROCESS FOR MAKING THE SAME, by T. J. Stokes et al., and granted Jan. 12, 1999 (attorney docket No. 12,232); the entire disclosure of which is incorporated herein by reference in a manner that is consistent herewith.

The complementary components of the mechanical fastener are configured to provide a selected attachment peel-force value. In a particular aspect, the peel-force value can be at least a minimum of about 75 grams (g). The peel-force value can alternatively be at least about 100 g, and can optionally be at least about 150 g to provide improved performance. In other aspects, the peel-force value can be up to a maximum of about 300 g, or more. The peel-force value can alternatively be up to about 250 g, and can optionally be up to about 225 g to provide improved effectiveness.

The complementary components of the mechanical fastener are also configured to provide a selected attachment shear-force value. In a particular aspect, the shear-force value can be at least a minimum of about 1000 g. The shear-force value can alternatively be at least about 1250 g, and can optionally be at least about 1500 g to provide improved performance. In other aspects, the shear-force value can be up to a maximum of about 3500 g, or more. The shear-force value can alternatively be up to about 3000 g, and can optionally be up to about 2000 g to provide improved effectiveness.

If the peel-force and/or the shear-force are outside the desired values, the fasteners may experience premature unfastening, or may be too difficult to unfasten to remove the article 20 from an associated undergarment.

In the construction of the article 20, the various components may be assembled and held together with any operative securement mechanism or system. For example, the desired attachments or securements can include adhesive bonds, cohesive bonds, thermal bonds, ultrasonic bonds, pins, snaps, staples, rivets, stitches, welds, zippers, or the like, as well as combinations thereof.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

The invention claimed is:

1. An absorbent personal care article having a longitudinal direction, a transverse cross-direction, a longitudinal centerline, and a transverse centerline, the article comprising a deformation-control member which has a pair of longitudinally-opposed half-portions positioned on opposite sides of the transverse centerline, a medial section, spaced along an entire length of the longitudinal and transverse centerline and a stiffened region;

the article, when in its plan view condition, having a configuration wherein said stiffened region includes a first array of individual, stiffening elements, and at least a second, differently arranged non-intersecting array of individual, stiffening elements;

said first array of stiffening elements is located only in a corresponding first, longitudinal half-portion of the deformation-control member and has a first, convergently arranged nose-end, and a first, relatively divergently arranged tail-end;

said first nose-end of the first array is positioned toward a central region of the article, said first tail-end of the first array is positioned to diverge toward a first longitudinal end region of the article, at an angle with the nose-end and tail-end of the first array aligned along the longitudinal direction;

said first array of stiffening elements is configured to substantially avoid intersecting in said medial section of said deformation-control member;

said second array of stiffening elements is located in a corresponding second, longitudinal half-portion of the deformation-control member and has a second, convergently arranged nose-end, and a second, relatively divergently arranged tail-end;

said second nose-end of the second array is positioned toward the central region of the article, said second tail-end of the second array is positioned to diverge toward a second longitudinal end region of the article, with the nose-end and tail-end of the second array aligned along the longitudinal direction;

the second end region of the article is located longitudinal opposite the first end region of the article;

said second array of stiffening elements is configured to substantially avoid intersecting in said medial section of said deformation-control member; and said second array of stiffening elements have a counter-positioned configuration which is in a longitudinally opposed, oppositely aligned arrangement, relative to the first array of stiffening elements.

2. An article as recited in claim 1, wherein said first array of stiffening elements includes a first array of embossment elements; and said second array of stiffening elements includes a second array of embossment elements.

3. An article as recited in claim 1, wherein said deformation-control member is configured to provide at least a portion of an absorbent body.

4. An article as recited in claim 2, wherein said deformation-control member is configured to provide at least a shaping layer portion of said absorbent body.

5. An article as recited in claim 2, wherein said article further includes a baffle and a liquid permeable cover; and said absorbent body is sandwiched between said baffle end cover.

6. An article as recited in claim 1, wherein said medial section of said deformation-control member has a medial section width of at least a minimum of about 2 mm and not more than about 45 mm.

7. An article as recited in claim 5, wherein said medial section of said deformation-control member has a medial section length of at least a minimum of about 50 mm and not more than about 300 mm.

8. An article as recited in claim 1, wherein
said stiffening elements have a width dimension and a relatively longer length dimension; and
a majority of the stiffening elements are substantially continuous along their length.

9. An article as recited in claim 7, wherein at least some of the stiffening elements are discontinuous.

10. An article as recited in claim 8, wherein the discontinuous stiffening elements are located in an intermediate section of the article.

11. An article as recited in claim 1, wherein
the stiffened region provides a first fishbone array of embossment elements, and at least a second fishbone array of embossment elements; and
the second array of embossment elements are arranged in a longitudinally opposed, oppositely facing, counter-position relative to the first array of embossment elements.

12. An article as recited in claim 1, wherein
the first array of stiffening elements have a first alignment angle which is at least a minimum of about 15 degrees and not more than a maximum of about 75 degrees; and
the second array of stiffening elements have a second alignment angle which is at least a minimum of about 15 degrees and not more than a maximum of about 75 degrees.

13. An article as recited in claim 1, wherein
the first array of stiffening elements has a first base-side section and a first complementary-side section.

14. An article as recited in claim 12, wherein said base-side section and said complementary-side section are substantially mirror images of each other.

15. An article as recited in claim 1, wherein the stiffening elements include embossment elements having a depth which provides a caliper percentage of at least a minimum of about 25% and not more than a maximum of about 95%.

16. An article as recited in claim 1, wherein the stiffening elements have a length which is at least a minimum of about 10 mm and up to a maximum of about 70 mm.

17. An article as recited in claim 1, wherein the stiffening elements have a separation distance between immediately adjacent stiffening elements, and such separation distance is at least a minimum of about 0.5 mm and not more than a maximum of about 40 mm.

18. An article as recited in claim 1, wherein at least a portion of the stiffening elements are substantially linear.

19. An article as recited in claim 1, wherein at least a portion of the stiffening elements are substantially curvilinear.

20. An article as recited in claim 1, wherein said deformation-control member includes an absorbent body; said absorbent body has a relatively larger shaping layer and a relatively smaller supplemental layer; and said stiffening elements include embossment elements located in the shaping layer.

21. An article as recited in claim 19, wherein said supplemental layer is located adjacent a bodyside of the shaping layer.

22. An article as recited in claim 19, wherein said supplemental layer is located adjacent a garment-facing side of the shaping layer.

23. An article as recited in claim 19, wherein said absorbent body further includes a perimeter embossment located proximally adjacent at least a portion of a terminal, perimeter edge of the absorbent body.

24. An article as recited in claim 22, wherein said embossment elements substantially avoid intersecting the perimeter embossment.

25. An article as recited in claim 23, wherein said embossment elements include relatively outboard end sections which are curved to substantially avoid intersecting the perimeter embossment.

26. An absorbent article as recited in claim 1, wherein
said deformation-control member includes an absorbent body;
said first array of stiffening elements includes a first array of embossment elements; and
said second array of stiffening elements includes a second array of embossment elements;
said first array of embossment elements are located a first portion of said absorbent body;
said second array of embossment elements are located on a second portion of said absorbent body which is longitudinally opposed to said first portion of the absorbent body;
the first array of embossment elements have a first embossment alignment angle which is at least about 15 degrees and is not more than about 75 degrees;
the second array of embossment elements have a second embossment alignment angle which is at least about 15 degrees and is not more than about 75 degrees;
the first array of embossment elements have a first base-side section and a first complementary-side section, said first complementary-side section being substantially a mirror image of said first base-side section;
the second array of embossment elements have a second base-side section and a second complementary-side section, said second complementary-side section being substantially a mirror image of said second base-side section;
said first array of embossment elements thereby having a first fishbone configuration, and said second array of embossment elements thereby having a second fishbone configuration which is counter-positioned relative to the first array of embossment elements;
said first complementary-side section is laterally spaced-away from said first base-side section;
said second complementary-side section is laterally spaced-away from said second base-side section;
said first array of embossment elements avoid entering into the medial section of the absorbent body; and
said second array of embossment elements avoid entering into the medial section of the absorbent body.

* * * * *